(12) United States Patent
Chen et al.

(10) Patent No.: US 7,525,672 B1
(45) Date of Patent: Apr. 28, 2009

(54) EFFICIENT CHARACTERIZATION OF SYMMETRICALLY ILLUMINATED SYMMETRIC 2-D GRATINGS

(75) Inventors: Shuqiang Chen, Sunnyvale, CA (US); Guoguang Li, Fremont, CA (US)

(73) Assignee: n&k Technology, Inc., San Jose, CA (US)

( * ) Notice: Subject to any disclaimer, the term of this patent is extended or adjusted under 35 U.S.C. 154(b) by 78 days.

(21) Appl. No.: 11/305,449

(22) Filed: Dec. 16, 2005

(51) Int. Cl.
*G01B 11/24* (2006.01)
(52) U.S. Cl. ............... 356/625; 356/636; 250/559.22
(58) Field of Classification Search ......... 356/600–601, 356/604–605, 610–614, 625, 629–630, 634–636, 356/364–396; 250/559.22, 559.24; 702/76; 438/14–16
See application file for complete search history.

(56) References Cited

U.S. PATENT DOCUMENTS

| | | | | |
|---|---|---|---|---|
| 5,337,144 A | * | 8/1994 | Strul et al. | 356/503 |
| 5,337,146 A | * | 8/1994 | Azzam | 356/367 |
| 5,432,607 A | * | 7/1995 | Taubenblatt | 356/364 |
| 6,100,985 A | * | 8/2000 | Scheiner et al. | 356/630 |
| 6,448,097 B1 | * | 9/2002 | Singh et al. | 438/16 |
| 6,458,605 B1 | * | 10/2002 | Stirton | 438/7 |
| 6,724,475 B2 | * | 4/2004 | Benesch et al. | 356/237.4 |
| 6,775,015 B2 | * | 8/2004 | Bischoff et al. | 356/636 |
| 6,819,426 B2 | * | 11/2004 | Sezginer et al. | 356/401 |
| 6,891,626 B2 | * | 5/2005 | Niu et al. | 356/625 |
| 6,898,537 B1 | * | 5/2005 | McGahan | 702/76 |
| 2004/0078173 A1 | | 4/2004 | Bischoff et al. | 703/2 |

OTHER PUBLICATIONS

Moharam et al., "Stable implementation of the rigorous coupled-wave analysis for surface-relief gratings: enhanced transmittance matrix approach," vol. 12, No. 5/May 1995/J. Opt. Soc. Am. A., pp. 1077-1086.

Moharam et al., "Formulation for stable and efficient implementation of the rigorous coupled-wave analysis of binary gratings," J. Opt. Soc. Am. A/vol. 12, No. 5/May 1995, pp. 1068-1076.

Soon Ting Han et al., "Electromagnetic scattering of two-dimensional surface-relief dielectric gratings," Applied Optics, May 1, 1992/vol. 31, No. 13, pp. 2343-2352.

(Continued)

*Primary Examiner*—Sang Nguyen
(74) *Attorney, Agent, or Firm*—Lumen Patent Firm

(57) ABSTRACT

Methods and apparatus for optical characterization based on symmetry-reduced 2-D RCWA calculations are provided. The invention is applicable to gratings having a grating reflection symmetry plane. A sample can be illuminated at normal incidence or at a non-zero angle of incidence such that the plane of incidence is parallel to or identical with the symmetry plane. The diffracted field components are either symmetric or anti-symmetric with respect to the grating symmetry plane. This symmetry is exploited to provide a symmetry-reduced 2-D RCWA having reduced matrix dimension (by about a factor of two) that is mathematically equivalent to a conventional 2-D RCWA. For normal incidence on a grating having two reflection symmetry planes, a symmetry-reduced 2-D RCWA having reduced matrix dimension (by about a factor of four) is provided. This normal incidence RCWA can be used to approximately characterize a sample illuminated at non-normal incidence. Approximation accuracy can be improved by modifying either the grating depth or the grating refractive index.

42 Claims, 7 Drawing Sheets

OTHER PUBLICATIONS

Philippe Lalanne et al., "Highly improved convergence of the coupled-wave method for TM polarization," J. Opt. Soc. Am. A./vol. 13, No. 4/Apr. 1996, pp. 779-784.

Philippe Lalanne, "Improved formulation of the coupled-wave method for two-dimensional gratings," J. Opt. Soc. Am. A./vol. 14, No. 7/Jul. 1997, pp. 1592-1598.

* cited by examiner

EFFICIENT CHARACTERIZATION OF SYMMETRICALLY ILLUMINATED SYMMETRIC 2-D GRATINGS

CROSS REFERENCE TO RELATED APPLICATIONS

This application claims the benefit of U.S. application Ser. No. 10/940,243 filed on Sep. 13, 2004 and entitled "System and Method for Efficient Characterization of Diffracting Structures with Incident Plane Parallel to Grating Lines".

FIELD OF THE INVENTION

This invention relates to optical characterization of patterned structures.

BACKGROUND

Manufacturing processes for producing products usually rely on quantitative measurements to provide information required for process control. Such measurements can be made on the final product, and/or on intermediate stages of the product within the manufacturing process, and/or on tools/fixtures used in the manufacturing process. For example, in semiconductor chip fabrication, measurements can be performed on finished chips (i.e., final product), on a wafer patterned with a photoresist (i.e., intermediate stage), or on a mask (i.e., a tool or fixture). Frequently, as in the case of semiconductor chip fabrication, these measurements are performed on structures having small dimensions. Furthermore, it is highly desirable to perform process control measurements quickly and non-destructively, in order to ensure a minimal impact on the process being controlled. Since optical measurements can be performed quickly, tend to be non-destructive, and can be sensitive to small features, various optical process control measurements have been developed.

Optical process control measurements can often be regarded as methods for measuring parameters of a pattern. For example, a pattern can be a periodic one-dimensional or two-dimensional grating on the surface of a wafer, and the parameters to measure can include feature dimensions, feature spacings and depth of the grating. To measure these parameters, an optical response of the pattern is measured. For example, reflectance as a function of wavelength can be measured. Typically, the optical response will depend on the parameter (or parameters) of interest in a complicated way such that direct parameter extraction from measured data is impractical. Instead, a mathematical model is typically constructed for the pattern, having the parameters of interest as variables. Within the model, a modeled optical response is calculated corresponding to the measured optical response. The parameters of interest are then determined by adjusting the variables to fit the modeled response to the measured response. Various optical process control measurements differ depending on the measured response(s), and on the kind of mathematical model employed.

A commonly-employed modeling approach for grating diffraction, known as the rigorous coupled wave analysis (RCWA), is described by Moharam et al. in Journal of the Optical Society of America (JOSA), A12, n5, p 1068-1076, 1995. The RCWA was first introduced by K. Knop in JOSA, v68, p 1206, 1978, and was later greatly improved by Moharam et al. in the above-referenced article. Some implementations of the RCWA for 1-D gratings are described in U.S. Pat. No. 6,590,656, U.S. 6,483,580, U.S. 5,963,329, and U.S. 5,867,276. The RCWA has been extended to 2-D gratings e.g., as considered by Han et al., Applied Optics 31(13), pp 2343-2352, 1992; and by Lalanne in JOSA A 14(7), pp 1592-1598, 1997. The use of RCWA modeling for characterizing 2-D gratings is also considered in U.S. 2004/007173.

Since a grating is periodic, grating-diffracted optical fields can be expressed as a superposition of space harmonics, each space harmonic having a different spatial period. The RCWA proceeds by including a finite number of space harmonics in the analysis (e.g., M for a 1-D grating and MN for a 2-D grating). Increasing M or MN increases accuracy, but requires more computation time, while decreasing M or MN decreases computation time, but provides reduced accuracy. The space harmonics each correspond to a diffraction order, so in a typical 2-D case where positive diffraction orders 1 through $N_x$, negative diffraction orders $-1$ through $-N_x$, and zero order diffraction are to be included for the x-direction in a calculation, we have $M=2N_x+1$. Similarly $N=2N_y+1$ if $N_y$ positive and negative orders are included for the y direction.

The time required to perform numerical RCWA calculations is dominated by matrix operations having a calculation time on the order of $M^3$ for a 1-D grating or $(MN)^3$ for a 2-D grating. Accordingly, various special cases have been considered in the literature where calculation time can be reduced compared to a more general case without reducing accuracy.

For example, in the above-referenced article by Moharam et al., 1-D planar diffraction is identified as a special case of 1-D conical diffraction. In 1-D planar diffraction, the plane of incidence of the light on the grating is perpendicular to the grating lines, while in 1-D conical diffraction, the plane of incidence makes an arbitrary angle with respect to the grating lines. Moharam et al. show that a 1-D planar diffraction calculation for N orders requires less than half the computation time of a 1-D conical diffraction calculation for N orders. Moharam et al. also indicate that for 1-D planar diffraction from a symmetric 1-D grating, the matrices to be processed take on special forms (i.e., symmetric for lossless gratings and Hermitian for lossy gratings), which can reduce computation time. Thus, a 1-D planar diffraction geometry has typically been used for grating characterization based on RCWA calculations.

Another special case for characterization with RCWA calculations which has been considered is normal incident angle illumination of a symmetric 1-D grating, e.g., as considered in U.S. Pat. No. 6,898,537. This case is especially simple, since illumination with normal incident angle is a special case of planar diffraction (i.e., the polarization coupling of conical diffraction does not occur), and illumination with normal incident angle on a symmetric grating leads to symmetric positive and negative diffraction orders. Thus N positive orders, N negative orders and the zero order can be accounted for in this case with only M=N+1 space harmonics. To accomplish this, a specialized RCWA assuming normal incident angle with a symmetric grating is derived from the standard RCWA.

However, the approach of U.S. Pat. No. 6,898,537 requires illumination with normal incident angle on the grating, which leads to practical difficulties. For example, in the common case where the response of interest is a zero order reflection, normal incident angle illumination requires separation of the incident light from the zero order reflected light. Providing such separation (e.g., with a beam splitter) requires additional optical element(s), which undesirably increases system complexity.

A symmetry-reduced RCWA for a 1-D grating illuminated at off-normal incidence such that the plane of incidence is parallel to the grating lines is described by the present inventors in the above-referenced application Ser. No. 10/940,243. In this method, symmetry is exploited to account for N positive and N negative diffraction orders (and zero order diffraction) with N+1 space harmonics.

Since 2-D RCWA calculations tend to be more time consuming than 1-D RCWA calculations, methods of reducing calculation time are of special interest for the 2-D case. For example, the above-referenced U.S. 2004/0078173 application considers the use of a library for storing intermediate results for improving efficiency. However, exploiting symmetry to reduce 2-D RCWA calculation time does not appear to be considered in the prior art. Thus it would be an advance in the art to provide characterization of 2-D gratings with a symmetry-reduced RCWA having decreased calculation time compared to a conventional 2-D RCWA.

SUMMARY

The present invention provides methods and apparatus for optical characterization based on symmetry-reduced 2-D RCWA calculations. The invention is applicable to gratings having a grating reflection symmetry plane, such that the grating is invariant under reflection in the symmetry plane. In one embodiment of the invention, the sample is illuminated at normal incidence or at a non-zero angle of incidence such that the plane of incidence is parallel to or identical with the symmetry plane. Since this illumination is consistent with the grating symmetry, the various diffracted field components are either symmetric or anti-symmetric with respect to the grating symmetry plane. This symmetry is exploited to provide a symmetry-reduced 2-D RCWA having reduced matrix dimension that is mathematically equivalent to a conventional 2-D RCWA. For RCWA calculations including a large number of diffracted orders, the matrix dimension is reduced by about a factor of two.

In another embodiment of the invention, the grating has an additional reflection symmetry plane. For example, let the grating lie in the x-y plane and have reflection symmetry in both the x-z and y-z planes of an orthogonal Cartesian coordinate system. Normal incidence illumination of such a grating leads to diffracted field components which are symmetric or anti-symmetric with respect to both symmetry planes. This symmetry is exploited to provide a symmetry-reduced 2-D RCWA for normal incidence having reduced matrix dimension that is mathematically equivalent to a conventional 2-D RCWA. For RCWA calculations including a large number of diffracted orders, the matrix dimension is reduced by about a factor of four for normal incidence.

Other embodiments of the invention relate to use of a symmetry-reduced normal incidence RCWA calculation to provide approximate results for a grating having two symmetry planes and illuminated at a non-zero angle of incidence. The accuracy of this approximation can be improved by modifying either the grating depth or the grating refractive index to account for the effect of incident angle on optical path length.

BRIEF DESCRIPTION OF THE DRAWINGS

FIG. 2b shows a close up top view of an element of the grating of FIG. 2a.

FIG. 3b shows a close up top view of an element of the grating of FIG. 3a.

DETAILED DESCRIPTION

Figure 1:
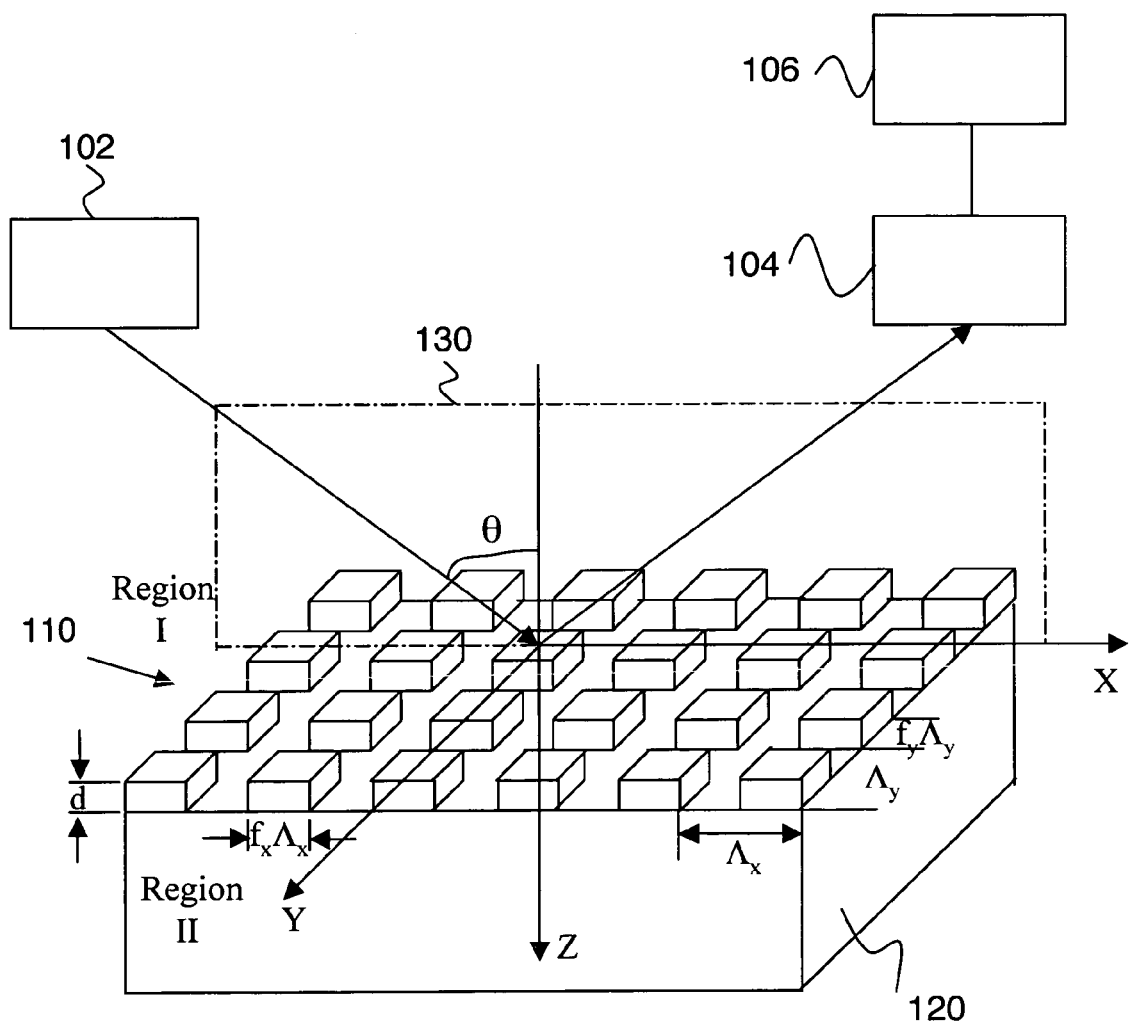
FIG. 1 shows an embodiment of the invention.

FIG. 1 shows an embodiment of the invention. An optical source 102 emits radiation toward a 2-D grating 110 on a substrate 120. Since grating 110 is 2-D, it has features which are arranged on a 2-D periodic lattice, which is assumed to have orthogonal lattice vectors. Coordinates are chosen as shown in FIG. 1, so grating 110 is in the x-y plane and has periods $\Lambda_x$ and $\Lambda_y$ in the x and y directions respectively. Grating 110 can have features of any shape, such as the rectangular features of FIGS. 2a-b or the circular features of FIGS. 3a-b. On FIGS. 2a-b, grating 200 has rectangular features 202 in unit cells 204. Features 202 have dimensions $f_x\Lambda_x$ and $f_y\Lambda_y$ in the x and y direction respectively. The permittivity and inverse permittivity matrices for rectangular feature gratings are given in Eqs. A11-A12. On FIGS. 3a-b, grating 300 has circular features 302 in unit cells 304. The permittivity and inverse permittivity matrices for circular feature gratings are given in Eqs. A35-A38c.

Grating 110 is assumed to be symmetric in a grating reflection plane 130, such that grating 110 is not changed by a geometrical reflection in plane 130. Effectively exploiting this symmetry of the grating is a key aspect of the invention. The light from source 102 is incident on grating 110 at normal incidence or at a non-zero angle of incidence θ. The plane of incidence (i.e., the plane containing the surface normal and the incident light wave vector) is parallel to (or identical with) the grating reflection plane 130. For normal incidence illumination, such alignment of the plane of incidence and the reflection plane is always possible. Equivalently, the incident optical wave vector lies within grating reflection plane 130 in all cases (i.e., both normal incidence and non-normal incidence). On FIG. 1, the x-z plane is both the plane of incidence and the grating reflection plane 130. By illuminating a symmetric 2-D grating in this manner, the overall symmetry of the physical situation is preserved, which is another key aspect of the invention. Since both normal incidence illumination and non-normal incidence illumination are included in the following description, it is convenient to define s and p polarization relative to reflection plane 130.

It is often convenient to regard grating 110 as separating region I having index $n_I$ from region II having index $n_{II}$. Although the example of FIG. 1 is a single-layer grating (also known as a binary grating), the invention is also applicable to multilayer or multi-region gratings, provided the appropriate symmetry conditions are met. Similarly, substrate 120 can include one or more uniform layers.

A detector 104 receives radiation diffracted by the grating. A processor 106 receives a measured response from detector 104 and provides a corresponding modeled response. Adjustment of parameters of the modeled response to achieve a good fit between the measured and modeled responses provides estimates of corresponding grating parameters. For example, these model/grating parameters can include feature width, feature length, feature radius, feature area, grating period (in either direction), grating depth (d on FIG. 1), or any other grating parameter. Preferably, source 102 can emit light at multiple wavelengths (either sequentially or simultaneously) and the response measured by detector 104 is zero order reflectance as a function of wavelength. The corresponding modeled response is also a zero order spectral reflectance. However, the invention can be also practiced by detecting any or all components of the diffracted beam, in reflection and/or in transmission, and calculating a modeled response corresponding to the measured response.

Processor 106, which can include any combination of hardware and/or software, performs a symmetry reduced 2-D RCWA calculation. The applicability of a symmetry reduced 2-D RCWA calculation is based on grating symmetry (i.e., reflection plane 130) and on symmetric illumination of the 2-D grating (i.e., reflection plane 130 is also the plane of incidence). Thus symmetry reduced 2-D RCWA methods are another key aspect of the invention. Symmetry reduced RCWA methods for 2-D gratings are best appreciated in connection with conventional 2-D grating RCWA methods. Accordingly, a mathematical development of both conventional and symmetry reduced 2-D RCWA methods is given in Appendix A. More specifically, Equations A-1 through A-38c relate to conventional 2-D RCWA calculations, while Equations A39-A54 relate to symmetry reduced RCWA methods in accordance with embodiments of the invention.

For a conventional 2-D RCWA including M diffraction orders in x and N diffraction orders in y, the matrix eigenvalue problem (e.g., as in Eq. A23) has matrix dimension 2MN. Thus if $M=2N_x+1$ and $N=2N_y+1$ (i.e., $N_x$ positive and negative diffracted orders are included for x and $N_y$ positive and negative orders are included for y), the conventional RCWA eigenvalue problem has matrix dimension $2(2N_x+1)(2N_y+1)$. In accordance with the invention, a symmetry-reduced RCWA can account for the same set of diffraction orders with an eigenvalue problem having matrix dimension $2(2N_x+1)(N_y+1)$ for non-normal incident light (e.g., as in Eqs. A42 and A45). For normal incidence, the matrix dimension can be further reduced, as described later.

Figure 4:
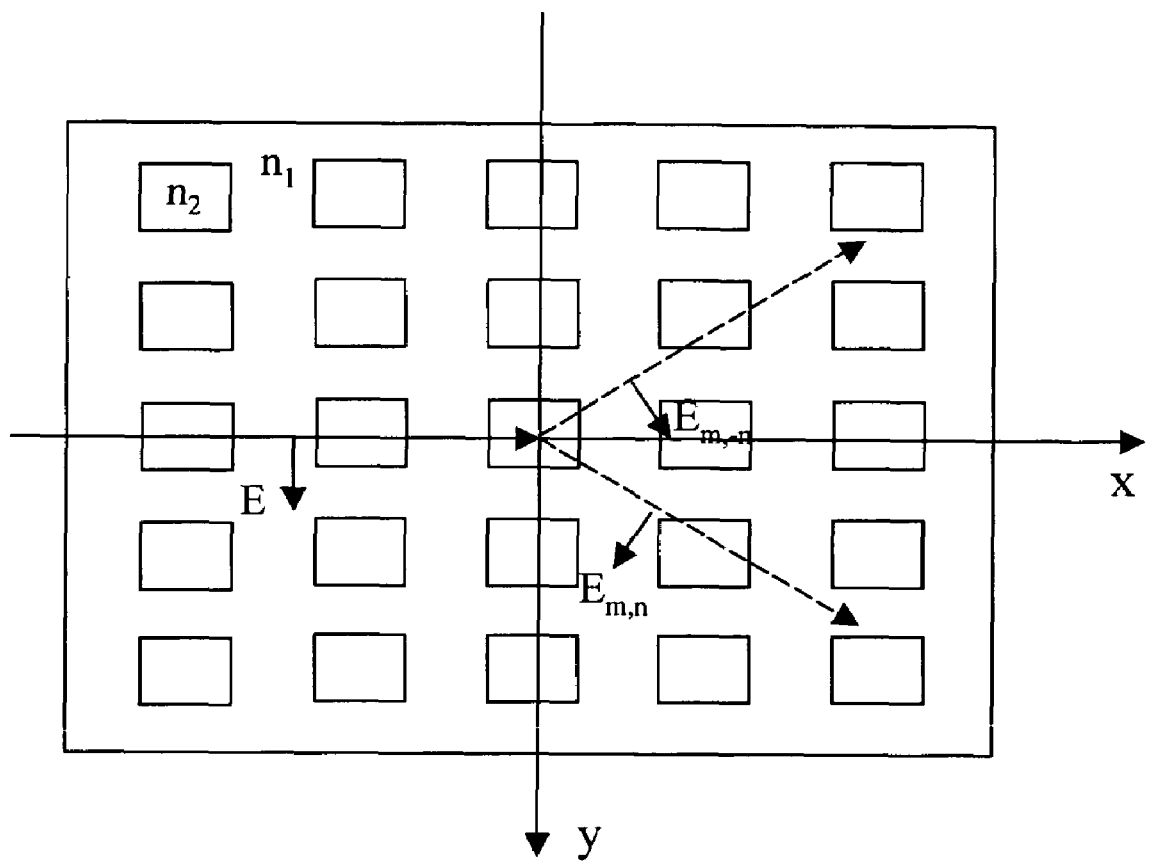
FIG. 4 shows symmetry of diffracted orders from a 2D grating illuminated at non-normal incidence in a symmetry plane of the grating.

This reduction of matrix dimension is best appreciated in connection with FIG. 4, which shows symmetry of diffracted orders from a 2D grating illuminated at non-normal incidence in a symmetry plane of the grating. More specifically, a top view of a 2-D grating illuminated with s-polarized light is shown, along with two diffracted rays having equal and opposite y-index. As shown on FIG. 4, the electric field y-components of the two diffracted rays are equal, while the electric field x-components of the two diffracted rays have equal magnitude and opposite sign. This symmetry is exact for plane-wave illumination and is a good approximation for illumination with a finite-width beam.

In view of these two possibilities (symmetry or antisymmetry) it is convenient to define matrix reduction rules as follows. A positive reduction rule $R^+$ is given by $$R_{mn,pq}^+ = F_{mn,pq} + F_{mn,p(-q)} \text{ for } q \neq 0, \text{ and} \tag{1a}$$

$$R_{mn,p0}^+ = F_{mn,p0} \text{ for } q=0, \tag{1b}$$

where $-N_x \leq m,p \leq N_x$, $0 \leq n,q \leq N_y$. A negative reduction rule $R^-$ is given by $$R_{mn,pq}^- = F_{mn,pq} - F_{mn,p(-q)} \text{ for } q \neq 0, \text{ and} \tag{2a}$$

$$R_{mn,p0}^- = F_{mn,p0} \text{ for } q=0. \tag{2b}$$

In these equations, F is a full matrix having dimension $(2N_x+1)(2N_y+1)$, and $R^+$ (or $R^-$) is a corresponding reduced matrix having dimension $(2N_x+1)(N_y+1)$. Such reduction in matrix size is a key advantage of the invention, since it significantly reduces RCWA calculation time.

Thus in the s-polarized example of FIG. 4, y-component electric field matrices (i.e., $R_y$, $T_y$, and $S_y$) and x-component magnetic field matrices (i.e., $U_x$) are reduced according to reduction rule $R^+$ and x-component electric field matrices (i.e., $R_x$, $T_x$, and $S_x$) and y-component magnetic field matrices (i.e., $U_y$) are reduced according to reduction rule $R^-$. Matrices for non-field quantities (e.g., permittivity E and inverse permittivity $E_{inv}$) are reduced using rules $R^+$ and/or $R^-$ as required to preserve mathematical equivalence to the conventional RCWA. For diagonal matrices (e.g., $K_x$ and $K_y$), rules $R^+$ and $R^-$ are equivalent. Details of this matrix reduction for s-polarization are given in Eqs. A39-A42, where Eq. A42 shows a reduced matrix eigenvalue problem having dimension $2(2N_x+1)(N_y+1)$.

Similarly, for p-polarized incident radiation y-component electric field matrices (i.e., $R_y$, $T_y$, and $S_y$) and x-component magnetic field matrices (i.e., $U_x$) are reduced according to reduction rule $R^-$ and x-component electric field matrices (i.e., $R_x$, $T_x$, and $S_x$) and y-component magnetic field matrices (i.e., $U_y$) are reduced according to reduction rule $R^+$. In this case as well, matrices for non-field quantities (e.g., wavenumbers $K_x$ and $K_y$, permittivity E, and inverse permittivity $E_{inv}$) are reduced using rules $R^+$ and/or $R^-$. Details of this matrix reduction for p-polarization are given in Eqs. A43-A45, where Eq. A45 shows a reduced matrix eigenvalue problem having dimension $2(2N_x+1)(N_y+1)$.

Preferably, light from source 102 is either s-polarized or p-polarized, so that RCWA matrix reduction can proceed as indicated above. This procedure is generally referred to as pre-selection of field components. However, the invention can also be practiced with incident light that has an unknown state or degree of polarization. In such cases, the incident light can be modeled as an appropriate combination of s and p polarized light.

Figure 5:
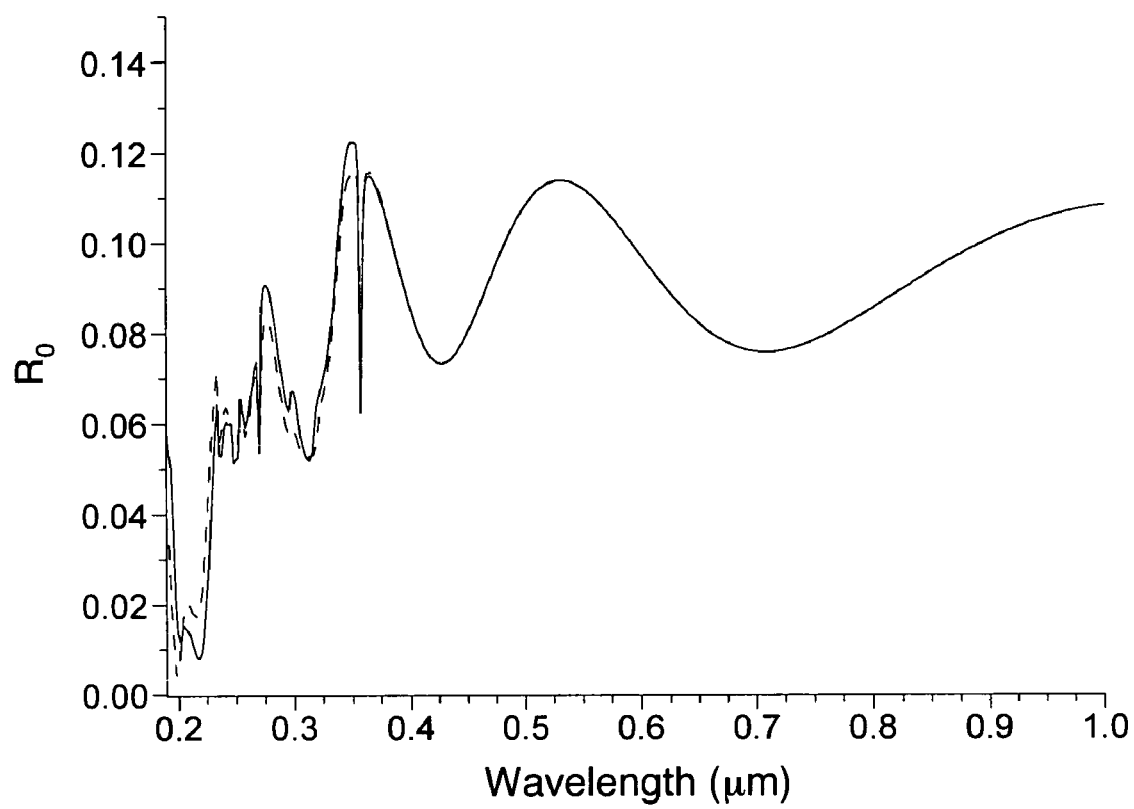
FIG. 5 shows examples of zero-order reflectances calculated according to embodiments of the invention.

FIG. 5 shows examples of zero-order reflectances calculated according to embodiments of the invention. The grating of this example is an $SiO_2$ grating having $\Lambda_x=\Lambda_y=300$ nm, $d=500$ nm, and $f_x=f_y=0.4$ on a substrate of $Si_3N_4$, and is illuminated from air with s-polarized light at $\theta=9°$. The solid line is a calculated zero order reflectivity using a reduced RCWA with pre-selection as described above. These results are identical to results from a conventional non-reduced RCWA. The dashed line shows results of a reduced RCWA without performing pre-selection (i.e., rule $R^+$ is used for all matrices). The difference between the results in these two cases tends to decrease as the number of space harmonics included in the analyses increases.

Further reduction of RCWA matrix size is possible for gratings which are illuminated at normal incidence and which have reflection symmetry in the y-z plane (in addition to the x-z reflection symmetry assumed above). In this special case, the x diffraction orders are related to each other by relations similar to those considered above for the y diffraction orders.

Figure 6:
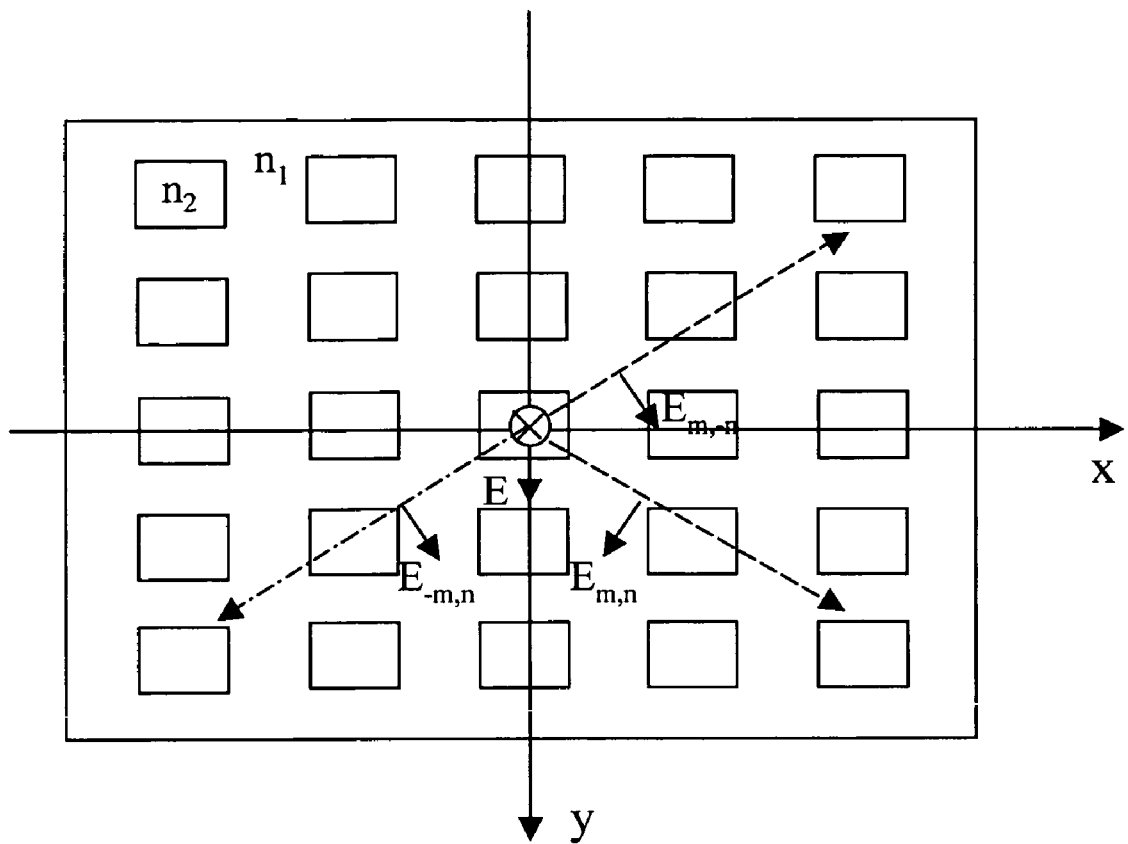
FIG. 6 shows symmetry of diffracted orders from a 2D grating illuminated at normal incidence.

FIG. 6 shows symmetry of diffracted orders from a 2D grating illuminated at normal incidence. For the normal incidence case, it is convenient to define s-polarized incident light as having an electric field in the y direction, while p-polarized incident light has an electric field in the x direction. Thus FIG. 6 shows s-polarized incident light along with some symmetry-related diffraction orders. As above, it is convenient to define matrix reduction rules. Since positive and negative matrix reductions can be performed for either x or y diffraction orders, we have four reduction rules.

For positive reduction in both x and y, rule $R^{++}$ is given by $$R_{mn,pq}^{++} = F_{mn,pq} + F_{mn,p(-q)} + F_{mn,(-p)q} + F_{mn,(-p)(-q)},$$

$$R_{mn,p0}^{++} = F_{mn,p0} + F_{mn,(-p)0},$$

$$R_{mn,0q}^{++} = F_{mn,0q} + F_{mn,0(-q)},$$

$$R_{mn,00}^{++} = F_{mn,00}, \tag{3a}$$

where $-N_x \leq m \leq N_x$, $-N_y \leq n \leq N_y$, $1 \leq p \leq N_x$, $1 \leq q \leq N_y$. For negative reduction in both x and y, rule $R^{--}$ is given by $$R_{mn,pq}^{--} = F_{mn,pq} - F_{mn,p(-q)} - F_{mn,(-p)q} + F_{mn,(-p)(-q)},$$

$$R_{mn,p0}^{--} = F_{mn,p0} - F_{mn,(-p)0},$$

$$R_{mn,0q}^{--} = F_{mn,0q} - F_{mn,0(-q)},$$

$$R_{mn,00}^{--} = F_{mn,00}, \tag{3b}$$

For positive reduction in x and negative reduction in y, rule $R^{+-}$ is given by $$R_{mn,pq}^{+-} = F_{mn,pq} - F_{mn,p(-q)} + F_{mn,(-p)q} - F_{mn,(-p)(-q)},$$

$$R_{mn,p0}^{+-} = F_{mn,p0} + F_{mn,(-p)0},$$

$$R_{mn,0q}^{+-} = F_{mn,0q} - F_{mn,0(-q)},$$

$$R_{mn,00}^{+-} = F_{mn,00}, \quad (3c)$$

For negative reduction in x and positive reduction in y, rule $R^{-+}$ is given by $$R_{mn,pq}^{-+} = F_{mn,pq} + F_{mn,p(-q)} - F_{mn,(-p)q} - F_{mn,(-p)(-q)},$$

$$R_{mn,p0}^{-+} = F_{mn,p0} - F_{mn,(-p)0},$$

$$R_{mn,0q}^{-+} = F_{mn,0q} + F_{mn,0(-q)},$$

$$R_{mn,00}^{-+} = F_{mn,00}, \quad (3d)$$

These reduction rules each relate a full matrix F having dimension $(2N_x+1)(2N_y+1)$ to a corresponding reduced matrix having dimension $(N_x+1)(N_y+1)$.

Pre-selection according to input polarization is preferred. Thus for s-polarized (i.e., y-polarized) incidence, electric field matrices reduce according to rule $R^{-+}$ and magnetic field matrices reduce according to rule $R^{+-}$. For p-polarized (i.e., x-polarized) incidence, electric field matrices reduce according to rule $R^{+-}$ and magnetic field matrices reduce according to rule $R^{-+}$. Other matrix quantities reduce according to rules $R^{++}$, $R^{--}$, $R^{+-}$, and/or $R^{-+}$ as indicated in Eqs. A46-A50 (s-polarization) and Eqs. A51-A54 (p-polarization).

Figure 7:
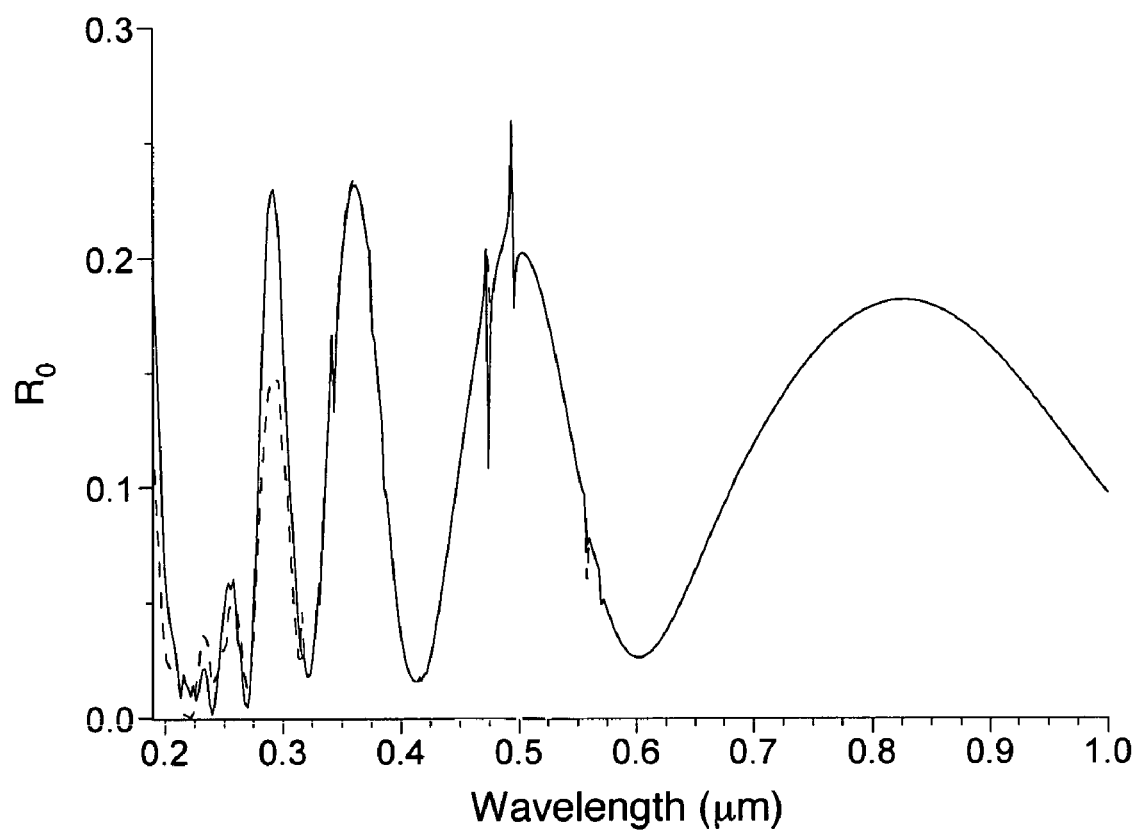
FIG. 7 shows examples of zero-order reflectances calculated according to embodiments of the invention.

FIG. 7 shows examples of zero-order reflectances calculated according to embodiments of the invention. The grating of this example is an $SiO_2$ grating having $\Lambda_x = \Lambda_y = 300$ nm, d=500 nm, and $f_x = f_y = 0.4$ on a two layer substrate of 300 nm of $Si_3N_4$ on $SiO_2$, and is illuminated from air with s-polarized light at normal incidence. The solid line is a calculated zero order reflectivity using a reduced RCWA with pre-selection for normal incidence as described above. These results are identical to results from a conventional non-reduced RCWA. The dashed line shows results of a reduced RCWA without performing pre-selection (i.e., rule $R^{++}$ is used for all matrices). The difference between the results in these two cases tends to decrease as the number of space harmonics included in the analyses increases.

Normal incidence symmetry reduction of an RCWA can be exploited for characterization in two different ways. The first way is to illuminate the sample under test at normal incidence and employ the corresponding symmetry reduced normal incidence RCWA. The second way is to illuminate the sample under test at a small non-normal angle of incidence, and use a symmetry-reduced normal incidence RCWA to approximately model this physical situation. In favorable cases, the resulting approximation errors are negligible. Since normal incidence illumination can be problematic in practice (e.g. the problem of separating reflected light from transmitted light arises), this second approach is of considerable interest. Optionally, modifications can be made to the grating depth or refractive index in order to improve the accuracy of the normal incidence angle approximation.

The modified d (or revised d) normal incident angle approximation is based on replacing d with $d \cdot \cos \theta$ in a symmetry reduced normal incidence RCWA. This approach ensures that the change in phase kd due to the off-normal incident angle is accounted for by altering d. For a simple binary grating (e.g., an air-Si grating), only the feature depth needs to be revised in this method, since the non-feature depth in this case has no independent significance. For gratings having multiple regions with different indices $n_i$ and the same depth d, an average $$\cos \overline{\theta} = \sum_i f_i \cdot \text{real}(n_i) \cdot \cos \theta_i \Big/ \sum_i f_i \cdot \text{real}(n_i) \quad (4)$$

is employed, where $\theta_i$ is defined by $n_i \sin \theta_i = n_I \sin \theta$ and $f_i$ is the filling factor for region i. Thus in this case, d is replaced with $d \cos \overline{\theta}$ in a symmetry reduced normal incidence RCWA.

Instead of revising the depth of the grating, it is also possible to revise its refractive indices to improve the accuracy of the normal incident angle approximation. The revised index approach is based on setting $n_i$ to $n_i \cos \theta_i$ for all materials (indexed by i) making up the grating structure (included the substrate) in a symmetry reduced normal incidence RCWA. Here the angles $\theta_i$ are propagation angles in each region as determined by Snell's law $n_i \sin \theta_i = n_I \sin \theta$. Each refractive index is revised to an "effective index" that provides the proper phase shift in the z-direction. The revised index approach is similar to the revised d approach, except that the cos ($\theta$) factors are applied to the indices instead of to the depth.

Further details and examples of these methods for improving the accuracy of normal incidence angle approximations are considered in connection with 1-D grating characterization in U.S. patent application Ser. No. 10/940,243 by the present inventors.

The preceding description has focused on RCWA matrix reductions based on symmetry, which is a key aspect of the invention. Since the invention is based on exploiting symmetry, it is applicable in conjunction with various modifications or refinements of the basic 2-D RCWA. For example, the invention is applicable to variants of the RCWA developed for multi-layer gratings (e.g., as considered in Eqs. A32-A34). For the single-layer or multi-layer gratings, RCWA efficiency can be improved by performing a partial calculation of only reflectances instead of a full calculation including both reflectances and transmittances, provided no transmittances are of interest.

The invention can also be employed in connection with the RCWA given by Lalanne to improve computational efficiency. Lalanne's method is based on an RCWA formalism where the relative contributions of the permittivity matrix E and the inverse permittivity matrix $E_{inv}$ to the RCWA are determined by an adjustable parameter $\alpha$. For 2-D rectangular gratings, $\alpha$ has a preferred value given by $f_y \Lambda_y / (f_x \Lambda_x + f_y \Lambda_y)$. The conventional RCWA development given in Eqs. A1-A34 includes Lalanne's $\alpha$ parameter, as do the examples of the present invention given in Eqs. A39-A54. Use of the Lalanne RCWA formalism is preferred but not required in practicing the invention.

Although exact symmetry is assumed to derive the various reduced RCWAs, the invention is not restricted to characterization of exactly symmetric gratings. Instead, it is sufficient for the grating to be substantially symmetric in the relevant symmetry plane or planes. The level of grating symmetry needed for sufficient accuracy will be application-dependent, and can be evaluated for particular applications by an art worker. In general terms, the required illumination symmetry for practicing the invention is that the incident optical wave vector be within a reflection symmetry plane of the 2-D grating. Both the off-normal incidence and normal incidence cases considered above are special cases of this wave vector geometry.

Appendix A

At first, we consider the diffraction of the 2D grating based on the rigorous RCWA method, which is described for the general case in the paper "Electromagnetic scattering of two-dimensional surface-relief dielectric gratings", by Soon Ting Han et al. in Applied Optics, vol. 31, no. 13, 2343-2352, 1992. For 2D gratings, we can always select the incident plane parallel to one of the grating lines. As shown in FIG. 1, consider the oblique incident beam (with angle θ) within x, z plane (which means the conical angle φ=0). In region I, the electric field of the incident beam is $$\vec{E}_{inc} = \vec{u} \exp(-j\vec{k}_1 \cdot \vec{r}) = \vec{u} \exp[-jk_0 n_1 (\sin\theta \cdot x + \cos\theta \cdot z)] \tag{A1}$$

where $$\vec{u} = \cos\psi \cos\theta \cdot \vec{e}_x + \sin\psi \cdot \vec{e}_y - \cos\psi \sin\theta \cdot \vec{e}_z \tag{A2}$$

$k_0 = 2\pi/\lambda$, $\lambda$ is the wavelength of light in free space, and $\psi=0°$, $90°$ corresponds to p (TM mode) and s (TE mode) polarization respectively. In regions I and II (cover and substrate), the normalized electric fields are $$\vec{E}_I = \vec{E}_{inc} + \sum_{m,n} \vec{R}_{m,n} \exp(-j\vec{k}_{I,mn} \cdot \vec{r}) \tag{A3}$$

$$\vec{E}_{II} = \sum_{m,n} \vec{T}_{m,n} \exp[-j\vec{k}_{II,mn}(\vec{r}-\vec{d})]. \tag{A4}$$

Here $\vec{R}_{m,n}$, $\vec{T}_{m,n}$ are the normalized mn order reflection (reflectance) and transmission field (transmittance) in I and II regions of FIG. 1, d is the depth of the grating, and m (range from 1 to M) and n (from 1 to N) are diffraction order number in x and y direction respectively.

In the grating region, the x, y components of the fields can be shown as the Fourier expression (z components are not independent)

$$E_x \vec{e}_x + E_y \vec{e}_y = \sum_{m,n} [S_{x,mn}(z)\vec{e}_x + S_{y,mn}(z)\vec{e}_y] \cdot \exp(-j\vec{\sigma}_{mn} \cdot \vec{r}) \tag{A5}$$

$$H_x \vec{e}_x + H_y \vec{e}_y = -j\sqrt{\frac{\varepsilon_0}{\mu_0}} \sum_{m,n} [U_{x,mn}(z)\vec{e}_x + U_{y,mn}(z)\vec{e}_y] \cdot \exp(-j\vec{\sigma}_{mn} \cdot \vec{r}) \tag{A6}$$

where $$\vec{\sigma}_{mn} = k_{xm} \vec{e}_x + k_{yn} \vec{e}_y = (k_{x0} - mK_x)\vec{e}_x + (k_{y0} - nK_y)\vec{e}_y \tag{A7}$$

$k_{x0} = k_0 n_I \sin\theta \cos\phi = k_0 n_I \sin\theta$, $k_{y0} = k_0 n_I \sin\theta \sin\phi = 0$; $K_x = 2\pi/\Lambda_x$, $K_y = 2\pi/\Lambda_y$, and $\Lambda_x$, $\Lambda_y$ are grating periods in x, y directions respectively. With the boundary conditions at z=0, z=d and by considering the zero order case m=n=0 in region I, we can find $$\vec{k}_{I,mn} = \vec{\sigma}_{mn} - k_{zI,mn} \vec{e}_z \tag{A8a}$$

$$\vec{k}_{II,mn} = \vec{\sigma}_{mn} + k_{zII,mn} \vec{e}_z \tag{A8b}$$

and $$k_{zl,mn} = \begin{cases} \sqrt{(k_0 n_l)^2 - k_{xm}^2 - k_{yn}^2}, & \text{Re}(k_{zl,mn}) > \text{Im}(k_{zl,mn}) \\ -j\sqrt{(k_0 n_l)^2 - k_{xm}^2 - k_{yn}^2}, & \text{Re}(k_{zl,mn}) < \text{Im}(k_{zl,mn}) \end{cases}, \tag{A9}$$

$l = I, II$

In the grating region, the relative permittivity and its inverse function can be written as $$\varepsilon(x,y) = \sum_{m,n} \varepsilon_{mn} \exp[j(mK_x x + nK_y y)] \tag{A10a}$$

$$\varepsilon(x,y)^{-1} = \sum_{m,n} a_{mn} \exp[j(mK_x x + nK_y y)] \tag{A10b}$$

For any given function $\epsilon(x,y)$, $\epsilon_{mn}$, $a_{mn}$ can be found.

For example, a 2D-grating with rectangular pixels has coefficients given by $$\varepsilon_{mn} = (n_2^2 - n_1^2) \frac{\sin(m\pi f_x)}{m\pi} \cdot \frac{\sin(n\pi f_y)}{n\pi} + n_1^2 \frac{\sin(m\pi)}{m\pi} \cdot \frac{\sin(n\pi)}{n\pi}. \tag{A11}$$

Here $n_1$, $n_2$ are refractive index of the two materials within the grating, and $f_x$, $f_y$ are the filling factor of $n_2$ in the period $\Lambda_x$, $\Lambda_y$ separately. The coefficient of its inverse function is:

$$a_{mn} = \left(\frac{1}{n_2^2} - \frac{1}{n_1^2}\right) \frac{\sin(m\pi f_x)}{m\pi} \cdot \frac{\sin(n\pi f_y)}{n\pi} + \frac{1}{n_1^2} \frac{\sin(m\pi)}{m\pi} \cdot \frac{\sin(n\pi)}{n\pi} \tag{A12}$$

With the Fourier expression, the Maxwell equations for the field in the grating region can be expressed in matrix form (as in the paper "*Highly improved convergence of the coupled-wave method for TM polarization*" by Philippe Lalanne et al in JOSA A, Vol. 13 Issue 4, p. 779, 1996).

$$\frac{\partial}{\partial z'} \begin{pmatrix} S_y \\ S_x \\ U_y \\ U_x \end{pmatrix} = \tag{A13}$$

$$\begin{pmatrix} 0 & 0 & K_y E^{-1} K_x & I - K_y E^{-1} K_y \\ 0 & 0 & K_x E^{-1} K_x - I & -K_x E^{-1} K_y \\ K_x K_y & E_{inv}^{-1} - K_y^2 & 0 & 0 \\ K_x^2 - E & -K_x K_y & 0 & 0 \end{pmatrix} \begin{pmatrix} S_y \\ S_x \\ U_y \\ U_x \end{pmatrix}$$

Here matrices E(mn, pq) and $E_{inv}$(mn, pq) are constructed by the element $\epsilon_{m-p,n-q}$, $a_{m-p,n-q}$ respectively, $z'=z/k_0$, $K_x$ is a diagonal MN×MN matrix with elements of $K_x(mn,mn)=k_{xm}$; and $K_y$ is a diagonal MN×MN matrix with elements of $K_y(mn,mn)=k_{yn}$; for $n=-N_x, \ldots, 0, \ldots, N_x$ ($N=2N_x+1$), $m=-N_y, \ldots, 0, \ldots, N_y$ ($M=2N_y+1$).

For improving convergence rate, eq. (A13) can be re-written (as in the paper "*Improved formulation of the coupled-wave method for two-dimensional gratings*" by Philippe Lalanne et al in JOSA A, 14 Issue 7, p. 1592, 1997)

$$\frac{\partial}{\partial z'}\begin{pmatrix} S_y \\ S_x \\ U_y \\ U_x \end{pmatrix} = B_A \cdot \begin{pmatrix} S_y \\ S_x \\ U_y \\ U_x \end{pmatrix}. \tag{A14}$$

Here $$B_A = \begin{pmatrix} 0 & B_1 \\ B_2 & 0 \end{pmatrix}, \tag{A15}$$

$$B_1 = \begin{pmatrix} K_y E^{-1} K_x & I - K_y E^{-1} K_y \\ K_x E^{-1} K_x - I & -K_x E^{-1} K_y \end{pmatrix}, \text{ and} \tag{A16}$$

$$B_2 = \begin{pmatrix} K_x K_y & \alpha E_{inv}^{-1} + (1-\alpha)E - K_y^2 \\ K_x^2 - \alpha E - (1-\alpha)E_{inv}^{-1} & -K_x K_y \end{pmatrix}, \tag{A17}$$

where $$\alpha = \frac{f_y \Lambda_y}{f_x \Lambda_x + f_y \Lambda_y} \tag{A18}$$

for 2D grating (and include the special case of $f_x=0$, $f_y=0$). For 1D grating or a uniform layer, $\alpha$ can be written as $$\alpha = \begin{cases} 1, & f_y = 1, f_x \neq 1 \\ 0, & f_y \neq 1, f_x = 1 \\ 1/2, & f_x = f_y = 1 \end{cases} \tag{A19}$$

Let $$S_t = \begin{pmatrix} S_y \\ S_x \end{pmatrix}, \quad U_t = \begin{pmatrix} U_y \\ U_x \end{pmatrix},$$

and then, $S_t$ can be expressed as Fourier series with its space harmonics $$S_{ti}(z) = \sum_{k=1}^{2MN} w_{ik}\{c_k^+ \exp(-k_0 q_k z) + c_k^- \exp[k_0 q_k (z-d)]\} \tag{A20a}$$

$$U_{ti}(z) = \sum_{k=1}^{2MN} v_{ik}\{-c_k^+ \exp(-k_0 q_k z) + c_k^- \exp[k_0 q_k (z-d)]\} \tag{A20b}$$

where $2MN=2\cdot M\cdot N$, and M, N are the maximum retained diffractive number in x, y direction separately. Here $i=1,\ldots,M\cdot N$ and $i=M\cdot N+1,\ldots,2\cdot M\cdot N$ corresponds to the $S_x$, $S_y$ separately. The eigenvalue equation can be written as $$A_B = B_1 B_2 \cdot W = W \cdot Q \tag{A21}$$

and $$V = B_2 \cdot W \cdot q^{-1} = B_1^{-1} W q \tag{A22}$$

where $$A_B = \begin{pmatrix} K_x^2 + D[\alpha E + (1-\alpha)E_{inv}^{-1}] & K_y\{E^{-1}K_x[\alpha E_{inv}^{-1} + (1-\alpha)E] - K_x\} \\ K_x\{E^{-1}K_y[\alpha E + (1-\alpha)E_{inv}^{-1}] - K_y\} & K_y^2 + B[\alpha E_{inv}^{-1} + (1-\alpha)E] \end{pmatrix}. \tag{A23}$$

Here $B=K_x E^{-1} K_x - I$, $D=K_y E^{-1} K_y - I$, and q is a diagonal matrix with the element $q_m$ ($q_m$=square root of the elements $Q_m$ in matrix Q).

Consider the field-amplitude vector and the corresponding wave vector in the cover and substrate region are orthogonal with each other $$\vec{k}_{I,mn} \cdot \vec{R}_{mn}=0, \quad \vec{k}_{II,mn} \cdot \vec{T}_{mn}=0 \tag{A24}$$

which leads to $$R_{zmn} = \frac{k_{xm} R_{xmn} + k_{yn} R_{ymn}}{k_{zI,mn}} \tag{A25a}$$

$$T_{zmn} = -\frac{k_{xm} T_{xmn} + k_{yn} T_{ymn}}{k_{zII,mn}}. \tag{A25b}$$

Combined with the Maxwell equations and the boundary conditions at the interface of the grating with regions I and II, we have $$\begin{pmatrix} D_1 \\ D_2 \end{pmatrix} + \begin{pmatrix} I \\ -jZ_I \end{pmatrix} R_t = \begin{pmatrix} W & WX \\ V & -VX \end{pmatrix} \begin{pmatrix} C^+ \\ C^- \end{pmatrix}, \tag{A26}$$

where $$D_1 = \begin{pmatrix} D_{1E} \\ D_{1M} \end{pmatrix}, \quad D2 = \begin{pmatrix} -jD_{2E} \\ jD_{2M} \end{pmatrix}, \quad R_t = \begin{pmatrix} R_y \\ R_x \end{pmatrix} \tag{A27}$$

are 2MN×1 matrices, and $$Z_I = \begin{pmatrix} -X_{yI} & -X_I \\ Y_I & X_{yI} \end{pmatrix} \tag{A28}$$

are 2MN×2MN matrices. Here $X_{yI}$ ia an MN×MN diagonal matrix with the diagonal elements of $k_{xm}k_{yn}/(k_{zI,mn}k_0)$, $X_I$ is a similar matrix having diagonal elements of $(k_{zI,mn}^2+k_{xm}^2)/(k_{zI,mn}k_0)$, $Y_I$ is a similar matrix having diagonal elements of $(k_{zI,mn}^2+k_{yn}^2)/(k_{zI,mn}k_0)$, $D_{1E}$, $D_{1M}$ are MN×1 matrices with the elements of $\sin\psi\delta_{m0}\delta_{n0}$, $\cos\psi\cos\theta\delta_{m0}\delta_{n0}$ respectively, and $D_{2E}$, $D_{2M}$ are MN×1 matrices with the elements of $n_I\cos\psi\delta_{m0}\delta_{n0}$, $n_I\cos\theta\sin\psi\delta_{m0}\delta_{n0}$.

At the boundary $z=d$, let $x_{yII}$ be an MN×MN diagonal matrix having diagonal elements of $k_{xm}k_{yn}/(k_{zII,mn}k_0)$, $X_{II}$ be a similar matrix having diagonal elements of $(k_{zII,mn}^2+k_{xm}^2)/(k_{zII,mn}k_0)$, and $Y_{II}$ be a similar matrix having diagonal elements of $(k_{zII,mn}^2+k_{yn}^2)/(k_{zII,mn}k_0)$. We can then find the matrix equation $$\begin{pmatrix} WX & W \\ VX & -V \end{pmatrix} \begin{pmatrix} C^+ \\ C^- \end{pmatrix} = \begin{pmatrix} I \\ jZ_{II} \end{pmatrix} T_t \quad \text{(A29)}$$

where $$T_t = \begin{pmatrix} T_y \\ T_x \end{pmatrix} \quad \text{(A30)}$$

is a 2MN×1 matrix, and where $$Z_{II} = \begin{pmatrix} -X_{yII} & -X_{II} \\ Y_{II} & X_{yII} \end{pmatrix} \quad \text{(A31)}$$

is a 2MN×2MN matrix. For a known grating structure and illuminated beam, the reflectance and transmittance can be found by solving Eqs. (A26), (A29).

For a multi-layer structure, $d_i (i=1, \ldots, L)$ are the thicknesses of each layer. At the boundary between $l-1$ and $l$ layers ($z=d_{l-1}$), the boundary condition can be written as the same form as for a 1D grating (described in the paper "Stable implementation of the rigorous coupled-wave analysis for surface-relief gratings: enhanced transmittance matrix approach" by M. G. Moharam et al in J. Opt. Soc. Amer. Vol. 12, no. 5, 1077, 1995), which gives $$\begin{pmatrix} W_{l-1}X_{l-1} & W_{l-1} \\ V_{l-1}X_{l-1} & -V_{l-1} \end{pmatrix} \begin{pmatrix} C_{l-1}^+ \\ C_{l-1}^- \end{pmatrix} = \begin{pmatrix} W_l & W_l X_l \\ V_l & -V_l X_l \end{pmatrix} \begin{pmatrix} C_l^+ \\ C_l^- \end{pmatrix}. \quad \text{(A32)}$$

In this case, Eqs. (A26), (A29) are re-written as $$\begin{pmatrix} D_1 \\ D_2 \end{pmatrix} + \begin{pmatrix} I \\ -jZ_I \end{pmatrix} R_t = \begin{pmatrix} W_1 & W_1 X_1 \\ V_1 & -V_1 X_1 \end{pmatrix} \begin{pmatrix} C_1^+ \\ C_1^- \end{pmatrix}, \text{ and} \quad \text{(A33)}$$

$$\begin{pmatrix} W_L X_L & W_L \\ V_L X_L & -V_L \end{pmatrix} \begin{pmatrix} C_L^+ \\ C_L^- \end{pmatrix} = \begin{pmatrix} I \\ jZ_{II} \end{pmatrix} T_t. \quad \text{(A34)}$$

Now, both $R_t$, $T_t$ can be found by solving above three equations.

Matrix of Dielectric of the 2D Grating with the Circle Media Interface

As shown in FIG. 3, in the grating region, relative permittivity and its inverse function can still be written as the same form in eq. (A10) since it is invariant in z direction. For the given function $\epsilon(x,y)$, $\epsilon_{mn}$, and $a_{mn}$ can be found. For the 2D circular pixel grating (with the periods $\Lambda_x$, $\Lambda_y$ in x, y directions), the coefficient can be calculated (by the similar method as rectangular grating) as:

$$\varepsilon_{mn} = \frac{1}{\Lambda_x \Lambda_y}(n_2^2 - n_1^2)I_{mn} \quad \text{(A35)}$$

where $$I_{mn} = \frac{\Lambda_y}{n\pi} \int_{-r}^{r} \exp\left(-j\frac{2m\pi}{\Lambda_x}x\right)\sin\left(\frac{2n\pi}{\Lambda_y}\sqrt{r^2-x^2}\right)dx. \quad \text{(A36)}$$

Since the coefficient of the inverse function of relative permittivity is similarly determined, we have $$\varepsilon_{mn} = \frac{2(n_2^2-n_1^2)}{n\pi\Lambda_x}\int_0^r \cos\left(\frac{2m\pi}{\Lambda_x}x\right)\sin\left(\frac{2n\pi}{\Lambda_y}\sqrt{r^2-x^2}\right)dx, \quad \text{(A37a)}$$

$$\varepsilon_{m0} = \frac{4(n_2^2-n_1^2)}{\Lambda_x\Lambda_y}\int_0^r \cos\left(\frac{2m\pi}{\Lambda_x}x\right)\sqrt{r^2-x^2}\,dx, \quad \text{(A37b)}$$

$$\varepsilon_{00} = (n_2^2-n_1^2)\frac{\pi r^2}{\Lambda_x\Lambda_y} + n_1^2, \quad \text{(A37c)}$$

and $$a_{mn} = \frac{2}{n\pi\Lambda_x}\left(\frac{1}{n_2^2}-\frac{1}{n_1^2}\right)\int_0^r \cos\left(\frac{2m\pi}{\Lambda_x}x\right)\sin\left(\frac{2n\pi}{\Lambda_y}\sqrt{r^2-x^2}\right)dx, \quad \text{(A38a)}$$

$$a_{m0} = \frac{4}{\Lambda_x\Lambda_y}\left(\frac{1}{n_2^2}-\frac{1}{n_1^2}\right)\int_0^r \cos\left(\frac{2m\pi}{\Lambda_x}x\right)\sqrt{r^2-x^2}\,dx, \quad \text{(A38b)}$$

$$a_{00} = \left(\frac{1}{n_2^2}-\frac{1}{n_1^2}\right)\frac{\pi r^2}{\Lambda_x\Lambda_y} + \frac{1}{n_1^2}, \quad \text{(A38c)}$$

Reduced Order in y

Figure 2A:
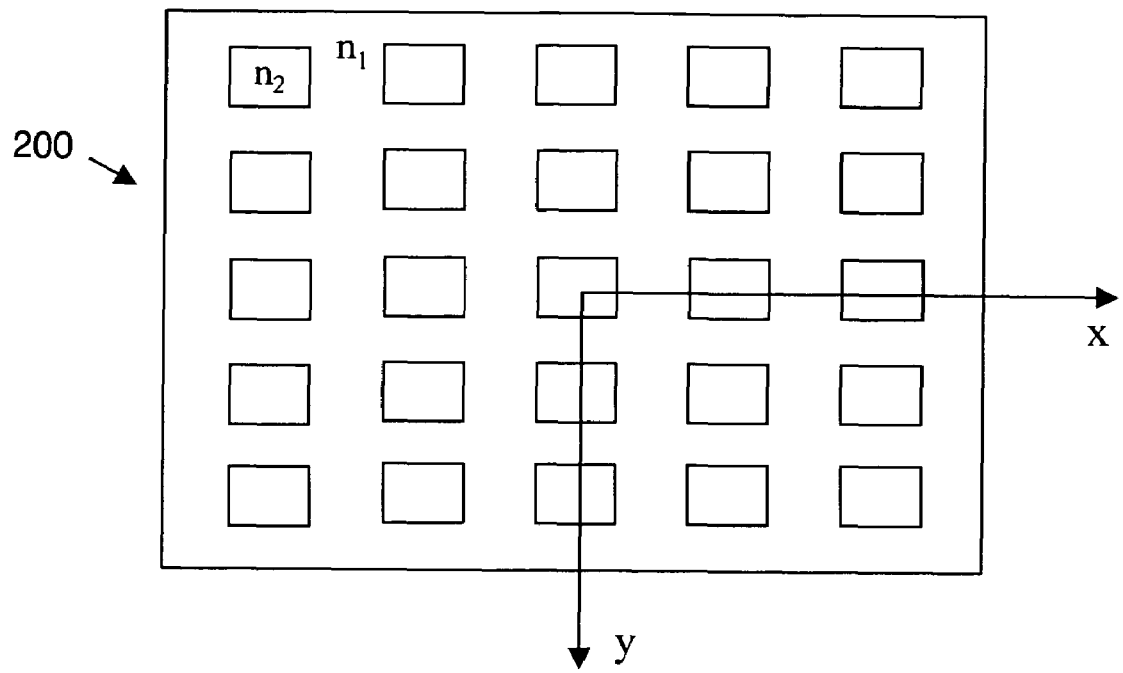
FIG. 2a shows a top view of a 2D grating having rectangular grating elements.
Figure 2B:
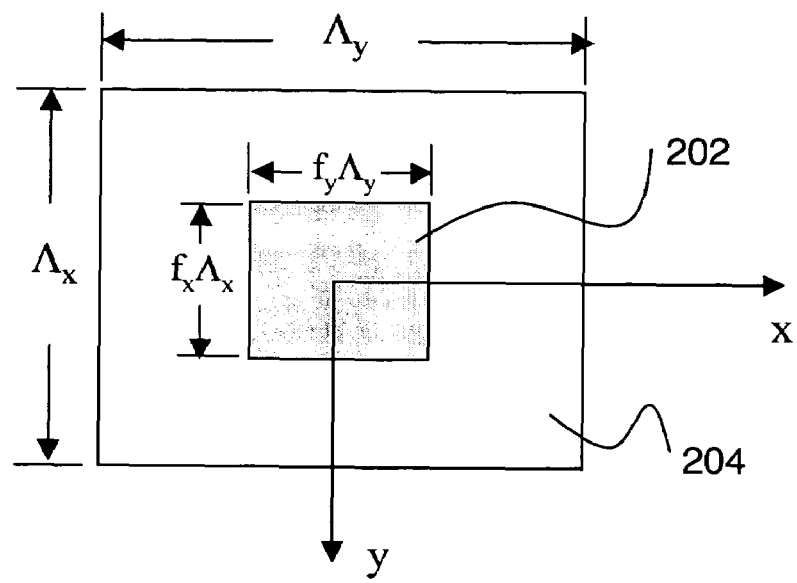
Figure 3A:
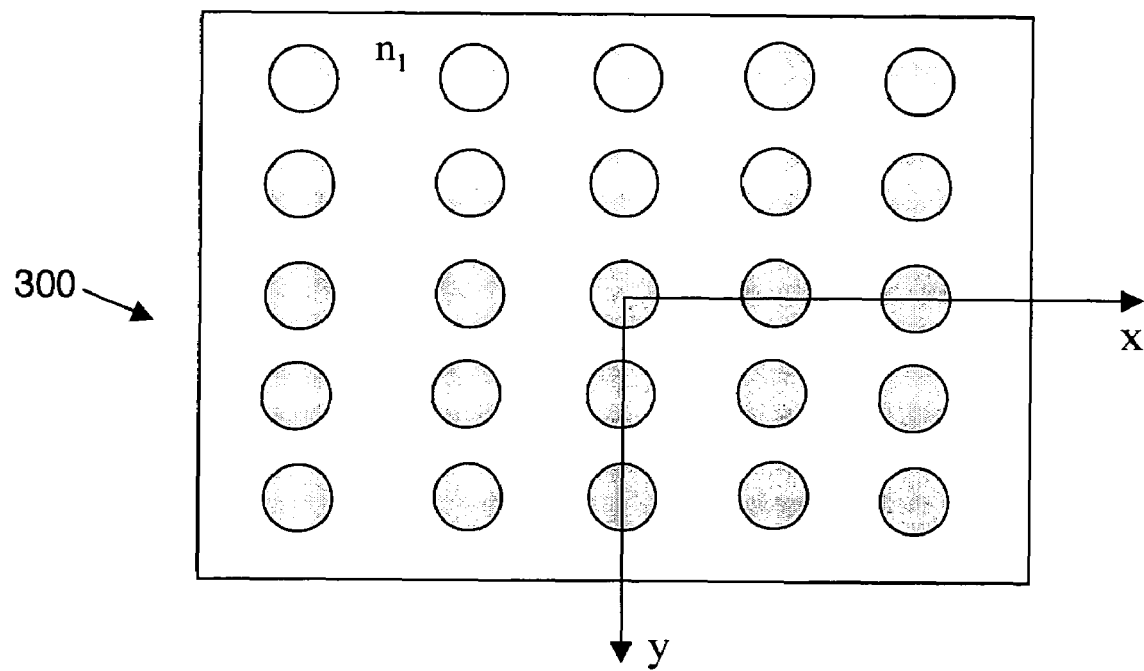
FIG. 3a shows a top view of a 2D grating having circular grating elements.
Figure 3B:
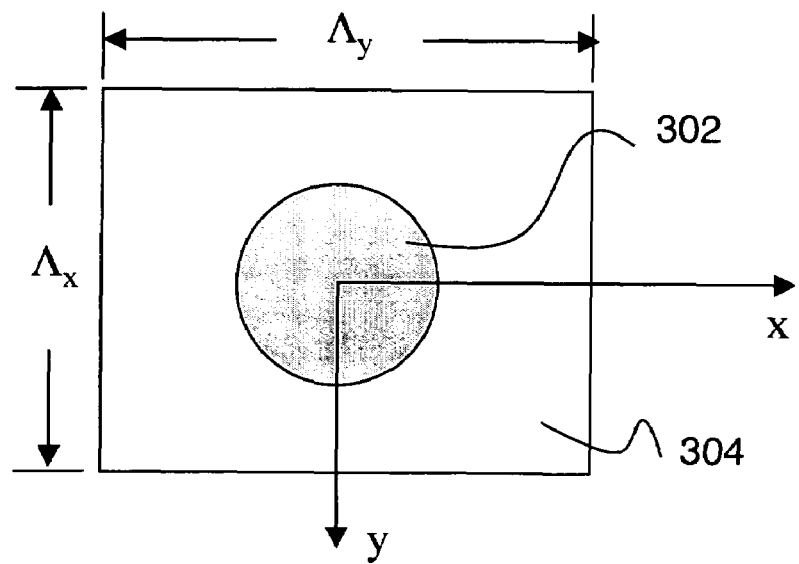

As shown in FIG. 1 and FIGS. 2a-b, both the grating and the illuminated beam are symmetric to y-axis. So the diffraction will also be symmetric. The total diffraction order MN (with $M=2N_x+1$, $N=2N_y+1$) problem can be changed to the reduced order $M(N_y+1)$ problem, where $N_x$, $N_y$ are positive diffraction order numbers in x, y direction separately.

In the case of 1D grating with normal incident beam, all the field component are symmetric (as shown in Nanometrics patent U.S. Pat. No. 6,898,537B1). The problem for non-normal incidence on a 2D grating is different. By tracing the rays of the diffraction within the grating layer (as in FIG. 4), we can find that the field components are symmetric or anti-symmetric in positive(n) and negative in y(−n) diffraction order depend on the different components and the polarization state of the incident beam.

For s-polarization ($\psi=90°$), in which the electric field of the incident beam is perpendicular with the incident plane (as in FIG. 1), $R_y$, $T_y$, $S_y$, $U_x$, $K_y$ are symmetric $$S_{y,m(-n)}=S_{y,mn}, U_{x,m(-n)}=U_{x,mn}$$

$$R_{y,m(-n)}=R_{y,mn}, T_{y,m(-n)}=T_{y,mn}, K_{y,m(-n)}=K_{y,mn} \quad \text{(A39)}$$

and $R_x$, $S_x$, $X_x$, $U_y$, $K_x$ are anti-symmetric $$S_{x,m(-n)}=-S_{x,mn}, U_{y,m(-n)}=-U_{y,mn}$$

$$R_{x,m(-n)}=-R_{x,mn}, T_{x,m(-n)}=-T_{x,mn}, K_{x,m(-n)}=-K_{x,mn} \quad \text{(A40)}$$

Similar to the 1D grating case (as considered in patent application Ser. No. 10/940,243 entitled "System and Method for Efficient Characterization of Diffracting Structures with Incident Plane Parallel to Grating Lines", filed Sep. 13, 2004 and assigned to Assignee of the present invention), a reduced $M(N_y+1)$ order matrix E with the symmetric and anti-symmetric field can be constructed by the following rules:

$$E_r^{mn,pq} = \begin{cases} E_{mn,pq} + E_{mn,p(-q)}, & q \neq 0 \\ E_{mn,p0}, & q = 0 \end{cases} \quad \text{(A41a)}$$

$$E_{-r}^{mn,pq} = \begin{cases} E_{mn,pq} - E_{mn,p(-q)}, & q \neq 0 \\ E_{mn,p0}, & q = 0 \end{cases} \quad \text{(A41b)}$$

-continued $$E_{r,inv}^{mn,pq} = \begin{cases} E_{inv}^{mn,pq} + E_{inv}^{mn,p(-q)}, & q \neq 0 \\ E_{inv}^{mn,p0}, & q = 0 \end{cases} \quad \text{(A41c)}$$

$$E_{-r,inv}^{mn,pq} = \begin{cases} E_{inv}^{mn,pq} - E_{inv}^{mn,p(-q)}, & q \neq 0 \\ E_{inv}^{mn,p0}, & q = 0 \end{cases} \quad \text{(A41d)}$$

With these transformations, all the related matrices developed from above matrices are all reduced in order from 2MN to $2M(N_y+1)$. The eigen matrix in eq. (A23) can be re-written as $$A_B = \begin{pmatrix} K_{xr}^2 + D_{-r}[\alpha E_r + (1-\alpha)E_{r,inv}^{-1}] & K_{yr}\{E_{-r}^{-1}K_{xr}[\alpha E_{-r,inv}^{-1} + (1-\alpha)E_{-r}] - K_{xr}\} \\ K_{xr}\{E_{-r}^{-1}K_{yr}[\alpha E_r + (1-\alpha)E_{r,inv}^{-1}] - K_{yr}\} & K_{yr}^2 + B_{-r}[\alpha E_{-r,inv}^{-1} + (1-\alpha)E_{-r}] \end{pmatrix} \quad \text{(A42)}$$

Here $B_{-r}=K_{xr}E_{-r}^{-1}K_{xr}-I_r$, $D_{-r}=K_{yr}E_{-r}^{-1}K_{yr}-I_r$, $I_r$ is the $M(N_y+1)$ order identity matrix, $K_{xr}$, $K_{yr}$ are $M(N_y+1)$ order diagonal matrices with $-N_y$ diffraction orders ignored.

For p-polarization ($\psi=0°$), $R_x$, $T_x$, $S_x$, $U_y$, $K_y$ are symmetric $$S_{x,m(-n)}=S_{x,mn}, U_{y,m(-n)}=U_{y,mn}$$

$$R_{x,m(-n)}=R_{x,mn}, T_{x,m(-n)}=T_{x,mn}, K_{y,m(-n)}=K_{y,mn} \quad \text{(A43)}$$

and $R_y$, $T_y$, $S_y$, $U_x$, $K_x$ are anti-symmetric $$S_{y,m(-n)}=-S_{y,mn}, U_{x,m(-n)}=-U_{x,mn}$$

$$R_{y,m(-n)}=-R_{y,mn}, T_{y,m(-n)}=-T_{y,mn}, K_{x,m(-n)}=-K_{x,mn} \quad \text{(A44)}$$

Eq. (A42) can be written as $$A_B = \begin{pmatrix} K_{xr}^2 + D_r[\alpha E_{-r} + (1-\alpha)E_{-r,inv}^{-1}] & K_{yr}\{E_r^{-1}K_{xr}[\alpha E_{r,inv}^{-1} + (1-\alpha)E_r] - K_{xr}\} \\ K_{xr}\{E_r^{-1}K_{yr}[\alpha E_{-r} + (1-\alpha)E_{-r,inv}^{-1}] - K_{yr}\} & K_{yr}^2 + B_r[\alpha E_{r,inv}^{-1} + (1-\alpha)E_r] \end{pmatrix} \quad \text{(A45)}$$

Here $B_r=K_{xr}E_r^{-1}K_{xr}-I_r$, and $D_r=K_{yr}E_r^{-1}K_{yr}-I_r$. The differences between Eq. (A45) and Eq. (A42) are only the exchanges of $E_r$ and $E_{-r}$, $E_{r,inv}$ and $E_{-r,inv}$, $B_r$ and $B_{-r}$, and $D_r$ and $D_{-r}$. The reflectance and transmittance of the diffraction can be found by solving the eigen problem of the reduced matrix $A_B$ and its boundary conditions (e.g., as shown in eq. (A33), (A34) for multi-layer gratings).

Normal Incidence

As shown in FIG. 6, the grating and the illuminated beam are symmetric in both x and y-directions. So the diffraction order will also be symmetric in both directions. The total diffraction order MN (with $M=2N_x+1$, $N=2N_y+1$) problem can be changed to a reduced order $(N_x+1)(N_y+1)$ problem. By tracing the rays of the diffraction within the grating layer (as in FIG. 6), we can find that the field components are symmetric or asymmetric in positive(m) and negative(-m) in x diffraction order as in the case of non-normal incident beam.

For s-polarization ($\psi=90°$), in which the electric field of the incident beam is perpendicular with the incident plane (as in FIG. 1), the field components $R_y$, $T_y$, $S_y$, $U_x$, $K_x$ are symmetric $$S_{y,(-m)n}=S_{y,mn}, U_{x,(-m)n}=U_{x,mn}$$

$$R_{y,(-m)n}=R_{y,mn}, T_{y,(-m)n}=T_{y,mn}, K_{y,(-m)n}=K_{y,mn} \quad \text{(A46)}$$

and $R_x$, $T_x$, $S_x$, $U_y$, $K_x$ are anti-symmetric $$S_{x,(-m)n}=-S_{x,mn}, U_{y,(-m)n}=-U_{y,mn}$$

$$R_{x,(-m)n}=-R_{x,mn}, T_{x,(-m)n}=-T_{x,mn}, K_{x,(-m)n}=-K_{x,mn} \quad \text{(A47)}$$

Now the reduced $(N_x+1)(N_y+1)$ order matrix of E with the symmetric and anti-symmetric fields can be reconstructed by the following rules:

$$E_{xy}^{mn,pq} = \quad \text{(A48a)}$$
$$\begin{cases} E_{mn,pq} + E_{mn,p(-q)} + E_{mn,(-p)q} + E_{mn,(-p)(-q)}, & p, q \neq 0 \\ E_{mn,p0} + E_{mn,(-p)0}, & p \neq 0, q = 0 \\ E_{mn,0q} + E_{mn,0(-q)}, & p = 0, q \neq 0 \\ E_{mn,00}, & p = q = 0 \end{cases}$$

-continued $$E_{-xy}^{mn,pq} = \quad \text{(A48b)}$$
$$\begin{cases} E_{mn,pq} - E_{mn,p(-q)} - [E_{mn,(-p)q} - E_{mn,(-p)(-q)}], & p, q \neq 0 \\ E_{mn,p0} - E_{mn,(-p)0}, & p \neq 0, q = 0 \\ E_{mn,0q} - E_{mn,0(-q)}, & p = 0, q \neq 0 \\ E_{mn,00}, & p = q = 0 \end{cases}$$

$$E_{x_-y}^{mn,pq} = \quad \text{(A48c)}$$
$$\begin{cases} E_{mn,pq} - E_{mn,p(-q)} + E_{mn,(-p)q} - E_{mn,(-p)(-q)}, & p, q \neq 0 \\ E_{mn,p0} + E_{mn,(-p)0}, & p \neq 0, q = 0 \\ E_{mn,0q} - E_{mn,0(-q)}, & p = 0, q \neq 0 \\ E_{mn,00}, & p = q = 0 \end{cases}$$

$$E_{y_-x}^{mn,pq} = \quad \text{(A48d)}$$
$$\begin{cases} E_{mn,pq} + E_{mn,p(-q)} - E_{mn,(-p)q} - E_{mn,(-p)(-q)}, & p, q \neq 0 \\ E_{mn,p0} - E_{mn,(-p)0}, & p \neq 0, q = 0 \\ E_{mn,0q} + E_{mn,0(-q)}, & p = 0, q \neq 0 \\ E_{mn,00}, & p = q = 0 \end{cases}$$

-continued $$E_{xy,inv}^{mn,pq} = \qquad (A48e)$$

$$\begin{cases} E_{inv}^{mn,pq} + E_{inv}^{mn,p(-q)} + E_{inv}^{mn,(-p)q} + E_{inv}^{mn,(-p)(-q)}, & p, q \neq 0 \\ E_{inv}^{mn,p0} + E_{inv}^{mn,(-p)0}, & p \neq 0, q = 0 \\ E_{inv}^{mn,0q} + E_{inv}^{mn,0(-q)}, & p = 0, q \neq 0 \\ E_{mn,00}, & p = q = 0 \end{cases}$$

$$E_{-xy,inv}^{mn,pq} = \qquad (A48f)$$

$$\begin{cases} E_{inv}^{mn,pq} - E_{inv}^{mn,p(-q)} - [E_{inv}^{mn,(-p)q} - E_{inv}^{mn,(-p)(-q)}], & p, q \neq 0 \\ E_{inv}^{mn,p0} - E_{inv}^{mn,(-p)0}, & p \neq 0, q = 0 \\ E_{inv}^{mn,0q} - E_{inv}^{mn,0(-q)}, & p = 0, q \neq 0 \\ E_{mn,00}, & p = q = 0 \end{cases}$$

Eqs. (A13)-(A17) can further be written as $$\frac{\partial S_y}{\partial z'} = K_{yN} E_{x\_y}^{-1} K_{xN} U_y + (I_N - K_{yN} E_{x\_y}^{-1} K_{yN}) U_x \qquad (A49a)$$

-continued $$\frac{\partial S_x}{\partial z'} = (K_{xN} E_{x\_y}^{-1} K_{xN} - I_N) U_y - K_{yN} E_{x\_y}^{-1} K_{yN} U_x \qquad (A49b)$$

$$\frac{\partial U_y}{\partial z'} = K_{yN} K_{xN} S_y + [\alpha E_{xy,inv}^{-1} + (1-\alpha) E_{\_xy} - K_{yN}^2] S_x \qquad (A49c)$$

$$\frac{\partial U_x}{\partial z'} = [K_{xN}^2 - \alpha E_{xy} - (1-\alpha) E_{xy,inv}^{-1}] S_y - K_{xN} K_{yN} S_x \qquad (A49d)$$

The related eigen matrix, corresponding to eq. (A23), (A42) can be re-written as $$A_B = \begin{pmatrix} K_{xN}^2 + D_{x\_y}[\alpha E_{xy} + (1-\alpha) E_{xy,inv}^{-1}] & K_{yN}\{E_{x\_y}^{-1} K_{xN}[\alpha E_{\_xy,inv}^{-1} + (1-\alpha) E_{\_xy}] - K_{xN}\} \\ K_{xN}\{E_{x\_y}^{-1} K_{yN}[\alpha E_{xy} + (1-\alpha) E_{xy,inv}^{-1}] - K_{yN}\} & K_{yN}^2 + B_{x\_y}[\alpha E_{xy,inv}^{-1} + (1-\alpha) E_{\_xy}] \end{pmatrix} \qquad (A50)$$

Here $B_{x\_y} = K_{xN} E_{x\_y}^{-1} K_{xN} - I_N$, $D_{x\_y} = K_{yN} E_{x\_y}^{-1} K_{yN} - I_N$, and $I_N$ is the identity matrix with $(N_x+1)(N_y+1)$ orders. $K_{xN}$, $K_{yN}$ are $(M_y+1)(N_y+1)$ order diagonal matrices with $-N_x$, $-N_y$ diffraction orders ignored.

For p-polarization ($\psi=0°$), $R_x$, $T_x$, $S_x$, $U_y$, $K_y$ are symmetric $$S_{x,(-m)n} = S_{x,mn}, \quad U_{y,(-m)n} = U_{y,mn}$$

$$R_{x,(-m)n} = R_{x,mn}, \quad T_{x,(-m)n} = T_{x,mn}, \quad K_{y,(-m)n} = K_{y,mn} \qquad (A51)$$

and $R_y$, $T_y$, $S_y$, $U_x$, $K_x$ are anti-symmetric $$S_{y,(-m)n} = -S_{y,mn}, \quad U_{x,(-m)n} = -U_{x,mn}$$

$$R_{y,(-m)n} = -R_{y,mn}, \quad T_{y,(-m)n} = -T_{y,mn}, \quad K_{x,(-m)n} = -K_{x,mn} \qquad (A52)$$

Eq. (A49) can be written as $$\frac{\partial S_y}{\partial z'} = K_{yN} E_{y\_x}^{-1} K_{xN} U_y + (I_N - K_{yN} E_{y\_x}^{-1} K_{yN}) U_x \qquad (A53a)$$

$$\frac{\partial S_x}{\partial z'} = (K_{xN} E_{y\_x}^{-1} K_{xN} - I_N) U_y - K_{xN} E_{y\_x}^{-1} K_{yN} U_x \qquad (A53b)$$

$$\frac{\partial U_y}{\partial z'} = K_{yN} K_{xN} S_y + [\alpha E_{xy,inv}^{-1} + (1-\alpha) E_{xy} - K_{yN}^2] S_x \qquad (A53c)$$

$$\frac{\partial U_x}{\partial z'} = [K_{xN}^2 - \alpha E_{xy} - (1-\alpha) E_{xy,inv}^{-1}] S_y - K_{xN} K_{yN} S_x \qquad (A53d)$$

The reduced matrices of $E_{xy}$, $E_{x\_y}$, $E_{\_xy}$, $E_{y\_x}$, $E_{xy,inv}$, $E_{\_xy,inv}$ are shown in Eq. (A48). Similarly, the eigen matrix as in eq. (A45) can be re-written as the $2(N_x+1)(N_y+1)$ form $$A_B = \begin{pmatrix} K_{xN}^2 + D_{y\_x}[\alpha E_{\_xy} + (1-\alpha) E_{\_xy,inv}^{-1}] & K_{yN}\{E_{y\_x}^{-1} K_{xN}[\alpha E_{xy,inv}^{-1} + (1-\alpha) E_{xy}] - K_{xN}\} \\ K_{xN}\{E_{y\_x}^{-1} K_{yN}[\alpha E_{\_xy} + (1-\alpha) E_{\_xy,inv}^{-1}] - K_{yN}\} & K_{yN}^2 + B_{y\_x}[\alpha E_{xy,inv}^{-1} + (1-\alpha) E_{xy}] \end{pmatrix} \qquad (A54)$$

Here $B_{y\_x} = K_{xN} E_{y\_x}^{-1} K_{xN} - I_N$, and $D_{y\_x} = K_{yN} E_{y\_x}^{-1} K_{yN} - I_N$. The reflectance and transmittance of different diffraction orders can be found by solving the eigen problem of the reduced matrix $A_B$ and its boundary condition as in Eqs. (A26)~(A34). For this normal incidence case, all of the matrices in these equations are reduced to order $2(N_x+1)(N_y+1)$.

What is claimed is:

1. A system for optically determining one or more parameters of a 2-D grating having substantial reflection symmetry in a grating reflection plane, the system comprising:
   a) an optical source providing optical radiation at a variable wavelength and illuminating said 2-D grating, wherein said radiation has a wave vector in said reflection plane;
   b) an optical detector receiving radiation from said 2-D grating and providing a measured spectral response; and
   c) a processor receiving said measured spectral response and providing a modeled spectral response of said 2-D grating having said parameters as variables, wherein said processor determines said one or more parameters by adjusting said variables to fit said modeled spectral response to said measured spectral response;
   wherein said modeled spectral response is provided by a symmetry-simplified rigorous coupled wave analysis (RCWA);
   wherein said grating is in an x-y plane, wherein said reflection plane is an x-z plane, wherein said RCWA accounts for $N_x$ positive diffraction orders and $N_x$ negative diffraction orders in the x direction, and wherein said RCWA accounts for $N_y$ positive diffraction orders and $N_y$ negative diffraction orders in the y direction;

wherein said grating reflection plane is perpendicular to a plane in which said 2-D grating is disposed.

2. The system of claim 1, wherein said RCWA is expressed in terms of a permittivity matrix E and an inverse permittivity matrix $E_{inv}$, and wherein relative contributions of E and $E_{inv}$ to said RCWA are determined by an adjustable parameter $\alpha$.

3. The system of claim 2, wherein said grating has a fill factor $f_x$ and a period $\Lambda_x$ in a direction parallel to said reflection plane and has a fill factor $f_y$ and a period $\Lambda_y$ in a direction perpendicular to said reflection plane, and wherein said parameter $\alpha$ is given by $\alpha = f_y \Lambda_y / (f_x \Lambda_x + f_y \Lambda_y)$.

4. The system of claim 1, wherein said symmetry-simplified RCWA comprises a symmetric RCWA having reduced matrices of dimension $(2N_x+1)(N_y+1)$.

5. The system of claim 4, wherein a positive matrix reduction relates a reduced matrix $R^+$ to a corresponding full matrix F as follows: $R_{mn,pq}{}^+ = F_{mn,pq} + F_{mn,p(-q)}$ for $q \neq 0$ and $R_{mn,p0}{}^+ = F_{mn,p0}$ for $q=0$, where $-N_x \leq m, p \leq N_x$, $0 \leq n, q \leq N_y$.

6. The system of claim 5, wherein said reduced matrices for all electric and magnetic field components are reduced according to said positive matrix reduction.

7. The system of claim 5, wherein a negative matrix reduction relates a reduced matrix $R^-$ to a corresponding full matrix F as follows: $R_{mn,pq}{}^- = F_{mn,pq} - F_{mn,p(-q)}$ for $q \neq 0$ and $R_{mn,p0}{}^- = F_{mn,p0}$ for $q=0$, where $-N_x \leq m, p \leq N_x$, $0 \leq n, q \leq N_y$.

8. The system of claim 7, wherein said optical radiation is s polarized relative to said reflection plane, wherein y-component electric field matrices and x-component magnetic field matrices in said RCWA are reduced according to said positive matrix reduction, and wherein x-component electric field matrices and y-component magnetic field matrices in said RCWA are reduced according to said negative matrix reduction.

9. The system of claim 7, wherein said optical radiation is p polarized relative to said reflection plane, wherein x-component electric field matrices and y-component magnetic field matrices in said RCWA are reduced according to said positive matrix reduction, and wherein y-component electric field matrices and x-component magnetic field matrices in said RCWA are reduced according to said negative matrix reduction.

10. The system of claim 1, wherein said grating is substantially reflection symmetric in a y-z plane, and wherein said symmetry-simplified RCWA comprises a normal incident angle RCWA having reduced matrices of dimension $(N_x+1)(N_y+1)$.

11. The system of claim 10, wherein a +− matrix reduction relates a reduced matrix $R^{+-}$ to a corresponding full matrix F as follows:

$R_{mn,pq}{}^{+-} = F_{mn,pq} - F_{mn,p(-q)} + F_{mn,(-p)q} - F_{mn,(-p)(-q)}$, $R_{mn,p0}{}^{+-} = F_{mn,p0} + F_{mn,(-p)0}$, $R_{mn,0q}{}^{+-} = F_{mn,0q} - F_{mn,0(-q)}$, $R_{mn,00}{}^{+-} = F_{mn,00}$, where $-N_x \leq m \leq N_x$, $-N_y \leq n \leq N_y$, $1 \leq p \leq N_x$, $1 \leq q \leq N_y$.

12. The system of claim 11, wherein a −+ matrix reduction relates a reduced matrix $R^{-+}$ to a corresponding full matrix F as follows:

$R_{mn,pq}{}^{-+} = F_{mn,pq} + F_{mn,p(-q)} - F_{mn,(-p)q} - F_{mn,(-p)(-q)}$, $R_{mn,p0}{}^{-+} = F_{mn,p0} - F_{mn,(-p)0}$, $R_{mn,0q}{}^{-+} = F_{mn,0q} + F_{mn,0(-q)}$, $R_{mn,00}{}^{-+} = F_{mn,00}$, where $-N_x \leq m \leq N_x$, $-N_y \leq n \leq N_y$, $1 \leq p \leq N_x$, $1 \leq q \leq N_y$.

13. The system of claim 12, wherein said incident radiation is y polarized and wherein electric field matrices in said RCWA are reduced according to said −+ matrix reduction and wherein magnetic field matrices in said RCWA are reduced according to said +− matrix reduction.

14. The system of claim 12, wherein said incident radiation is x polarized and wherein electric field matrices in said RCWA are reduced according to said +− matrix reduction and wherein magnetic field matrices in said RCWA are reduced according to said −+ matrix reduction.

15. The system of claim 10, wherein said grating separates region I having index $n_I$ from region II having index $n_{II}$, wherein said grating comprises two or more grating regions indexed by an integer i and having refractive indices $n_i$, and wherein said optical radiation is incident on said grating from said region I at a non-zero angle of incidence.

16. The system of claim 15, wherein said grating is a binary grating having features and trenches with indices $n_1$ and $n_2$ respectively, and having a grating depth d and a trench index $n_2 = n_I$, and wherein said normal incident angle RCWA comprises:
calculating a propagation angle $\theta_1$ for said features;
calculating a revised depth $d' = d \cos \theta_1$ for said grating; and
performing said normal incident angle RCWA using said revised depth $d'$ instead of said depth d.

17. The system of claim 15, wherein said grating has a grating depth d, wherein said grating regions each have a filling factor $f_i$, and wherein said normal incident angle RCWA comprises:
calculating a propagation angle $\theta_i$ in each of said grating regions;
calculating an average propagation angle $\bar{\theta}$ for said grating according to $$\cos \bar{\theta} = \sum_i f_i \cdot \text{real}(n_i) \cdot \cos \theta_i \bigg/ \sum_i f_i \cdot \text{real}(n_i);$$

calculating a revised depth $d' = d \cos \bar{\theta}$ for each of said grating regions; and
performing said normal incident angle RCWA using said revised depth $d'$ instead of said depth d.

18. The system of claim 15, wherein said normal incident angle RCWA comprises:
calculating a propagation angle $\theta_i$ for each of said grating regions;
calculating a propagation angle $\theta_{II}$ for said region II;
calculating a revised index $n_i' = n_i \cos \theta_i$ for each of said grating regions;
calculating a revised index $n_I' = n_I \cos \theta$ for said region I;
calculating a revised index $n_{II}' = n_{II} \cos \theta_{II}$ for said region II; and
performing said normal incident angle RCWA using said revised indices $n_I'$, $n_{II}'$, and $n_i'$, instead of $n_I$, $n_{II}$, and $n_i$ respectively.

19. The system of claim 1, wherein said grating is a multi-layer grating and wherein said symmetry-simplified RCWA comprises a multi-layer RCWA calculation.

20. The system of claim 19, wherein said multi-layer calculation comprises a partial calculation of the reflectance and not the transmittances.

21. The system of claim 1, wherein said optical radiation is a polarized, p polarized, or unpolarized with respect to said reflection plane.

22. The system of claim 1, wherein said parameters are selected from the group consisting of a feature width, a feature length, a feature radius, a feature area, a grating period in said reflection plane, a grating period perpendicular to said reflection plane, and a grating depth.

23. The system of claim 1, wherein said measured spectral response is a measured spectral reflectance and said modeled spectral response is a modeled spectral reflectance.

24. The system of claim 1, wherein said measured spectral response is a measured spectral transmittance and said modeled spectral response is a modeled spectral transmittance.

25. The system of claim 1, wherein said measured spectral response is a measured zero order spectral response and said modeled spectral response is a modeled zero order spectral response.

26. A method for optically determining one or more parameters of a 2-D grating having substantial reflection symmetry in a grating reflection plane, the method comprising:
   a) illuminating said 2-D grating with optical radiation, wherein said radiation has a wave vector in said reflection plane;
   b) providing a measured response of said 2-D grating by collecting radiation from said illuminated 2-D grating;
   c) providing a modeled response of said 2-D grating having said parameters as variables with a symmetry-simplified analysis; and
   d) determining said one or more parameters by adjusting said variables to fit said modeled response to said measured response;
   wherein said modeled spectral response is provided by a symmetry-simplified rigorous coupled wave analysis (RCWA);
   wherein said grating is in an x-y plane, wherein said reflection plane is an x-z plane, wherein said RCWA accounts for $N_x$ positive diffraction orders and $N_x$ negative diffraction orders in the x direction, and wherein said RCWA accounts for $N_y$ positive diffraction orders and $N_y$ negative diffraction orders in the y direction;
   wherein said grating reflection plane is perpendicular to a plane in which said 2-D grating is disposed.

27. The method of claim 26, wherein said RCWA is expressed in terms of a permittivity matrix E and an inverse permittivity matrix $E_{inv}$, and wherein relative contributions of E and $E_{inv}$ to said RCWA are determined by an adjustable parameter α.

28. The method of claim 26, wherein said symmetry-simplified RCWA comprises a symmetric RCWA having reduced matrices of dimension $(2N_x+1)(N_y+1)$.

29. The method of claim 28, wherein a positive matrix reduction relates a reduced matrix $R^+$ to a corresponding full matrix F as follows: $R_{mn,pq}^+ = F_{mn,pq} + F_{mn,p(-q)}$ for q≠0 and $R_{mn,p0}^+ = F_{mn,p0}$ for q=0, where $-N_x \leq m, p \leq N_x$, $0 \leq n, q \leq N_y$.

30. The method of claim 29, wherein said reduced matrices for all electric and magnetic field components are reduced according to said positive matrix reduction.

31. The method of claim 29, wherein a negative matrix reduction relates a reduced matrix $R^-$ to a corresponding full matrix F as follows: $R_{mn,pq}^- = F_{mn,pq} - F_{mn,p(-q)}$ for q≠0 and $R_{mn,p0}^- = F_{mn,p0}$ for q=0, where $-N_x \leq m, p \leq N_x$, $0 \leq n, q \leq N_y$.

32. The method of claim 31, wherein said optical radiation is s polarized relative to said reflection plane, wherein y-component electric field matrices and x-component magnetic field matrices in said RCWA are reduced according to said positive matrix reduction, and wherein x-component electric field matrices and y-component magnetic field matrices in said RCWA are reduced according to said negative matrix reduction.

33. The method of claim 31, wherein said optical radiation is p polarized relative to said reflection plane, wherein x-component electric field matrices and y-component magnetic field matrices in said RCWA are reduced according to said positive matrix reduction, and wherein y-component electric field matrices and x-component magnetic field matrices in said RCWA are reduced according to said negative matrix reduction.

34. The method of claim 26, wherein said grating is substantially reflection symmetric in a y-z plane, and wherein said symmetry-simplified RCWA comprises a normal incident angle RCWA having reduced matrices of dimension $(N_x+1)(N_y+1)$.

35. The method of claim 34, wherein a +− matrix reduction relates a reduced matrix $R^{+-}$ to a corresponding full matrix F as follows:

$$R_{mn,pq}^{+-} = F_{mn,pq} - F_{mn,p(-q)} + F_{mn,(-p)q} - F_{mn,(-p)(-q)},$$

$$R_{mn,p0}^{+-} = F_{mn,p0} + F_{mn,(-p)0},$$

$$R_{mn,0q}^{+-} = F_{mn,0q} - F_{mn,0(-q)},$$

$$R_{mn,00}^{+-} = F_{mn,00},$$

where $-N_x \leq m \leq N_x$, $-N_y \leq n \leq N_y$, $1 \leq p \leq N_x$, $1 \leq q \leq N_y$.

36. The method of claim 35, wherein a −+ matrix reduction relates a reduced matrix $R^{-+}$ to a corresponding full matrix F as follows:

$$R_{mn,pq}^{-+} = F_{mn,pq} + F_{mn,p(-q)} - F_{mn,(-p)q} - F_{mn,(-p)(-q)},$$

$$R_{mn,p0}^{-+} = F_{mn,p0} - F_{mn,(-p)0},$$

$$R_{mn,0q}^{-+} = F_{mn,0q} + F_{mn,0(-q)},$$

$$R_{mn,00}^{-+} = F_{mn,00},$$

where $-N_x \leq m \leq N_x$, $-N_y \leq n \leq N_y$, $1 \leq p \leq N_x$, $1 \leq q \leq N_y$.

37. The method of claim 36, wherein said incident radiation is y polarized and wherein electric field matrices in said RCWA are reduced according to said −+ matrix reduction and wherein magnetic field matrices in said RCWA are reduced according to said +− matrix reduction.

38. The method of claim 36, wherein said incident radiation is x polarized and wherein electric field matrices in said RCWA are reduced according to said +− matrix reduction and wherein magnetic field matrices in said RCWA are reduced according to said −+ matrix reduction.

39. The method of claim 34, wherein said grating separates region I having index $n_I$ from region II having index $n_{II}$, wherein said grating comprises two or more grating regions indexed by an integer i and having refractive indices $n_i$, and wherein said optical radiation is incident on said grating from said region I at a non-zero angle of incidence.

40. The method of claim 39, wherein said grating is a binary grating having features and trenches with indices $n_1$ and $n_2$ respectively, and having a grating depth d and a trench index $n_2 = n_I$, and wherein said normal incident angle RCWA comprises:
   calculating a propagation angle $\theta_1$ for said features;
   calculating a revised depth $d' = d \cos \theta_1$ for said grating; and
   performing said normal incident angle RCWA using said revised depth d' instead of said depth d.

41. The method of claim 39, wherein said grating has a grating depth d, wherein said grating regions each have a filling factor $f_i$, and wherein said normal incident angle RCWA comprises:
   calculating a propagation angle $\theta_i$ in each of said grating regions;

calculating an average propagation angle $\bar{\theta}$ for said grating according to $$\cos\bar{\theta} = \sum_i f_i \cdot \mathrm{real}(n_i) \cdot \cos\theta_i \Big/ \sum_i f_i \cdot \mathrm{real}(n_i);$$

calculating a revised depth $d'=d\cos\bar{\theta}$ for each of said grating regions; and performing said normal incident angle RCWA using said revised depth $d'$ instead of said depth $d$.

42. The method of claim 39, wherein said optical radiation is p-polarized and wherein said normal incident angle RCWA comprises:

calculating a propagation angle $\theta_i$ for each of said grating regions;

calculating a propagation angle $\theta_{II}$ for said region II;

calculating a revised index $n_i'=n_i\cos\theta_i$ for each of said grating regions;

calculating a revised index $n_I'=n_I\cos\theta$ for said region I;

calculating a revised index $n_{II}'=n_{II}\cos\theta_{II}$ for said region II; and performing said normal incident angle RCWA using said revised indices $n_I'$, $n_{II}'$, and $n_i'$, instead of $n_I$, $n_{II}$, and $n_i$ respectively.

* * * * *